US012251496B2

(12) United States Patent
Turng et al.

(10) Patent No.: US 12,251,496 B2
(45) Date of Patent: Mar. 18, 2025

(54) WAVY MULTI-COMPONENT VASCULAR GRAFTS WITH BIOMIMETIC MECHANICAL PROPERTIES, ANTITHROMBOGENICITY, AND ENDOTHELIAL CELL AFFINITY

(71) Applicant: Wisconsin Alumni Research Foundation, Madison, WI (US)

(72) Inventors: Lih-Sheng Turng, Madison, WI (US); Hao-Yang Mi, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1046 days.

(21) Appl. No.: 16/426,099

(22) Filed: May 30, 2019

(65) Prior Publication Data

US 2019/0365953 A1 Dec. 5, 2019

Related U.S. Application Data

(60) Provisional application No. 62/677,931, filed on May 30, 2018.

(51) Int. Cl.
| | |
|---|---|
| *A61L 27/50* | (2006.01) |
| *A61F 2/06* | (2013.01) |
| *A61L 27/18* | (2006.01) |
| *A61L 27/20* | (2006.01) |
| *A61L 27/24* | (2006.01) |
| *A61L 27/26* | (2006.01) |
| *A61L 27/38* | (2006.01) |
| *A61L 27/48* | (2006.01) |
| *B32B 5/26* | (2006.01) |
| *D01D 5/00* | (2006.01) |

(52) U.S. Cl.
CPC .............. *A61L 27/507* (2013.01); *A61F 2/06* (2013.01); *A61L 27/18* (2013.01); *A61L 27/20* (2013.01); *A61L 27/24* (2013.01); *A61L 27/26* (2013.01); *A61L 27/3808* (2013.01); *A61L 27/3826* (2013.01); *A61L 27/3834* (2013.01); *A61L 27/3886* (2013.01); *A61L 27/48* (2013.01); *B32B 5/26* (2013.01); *D01D 5/0007* (2013.01); *A61F 2210/0076* (2013.01); *A61F 2240/001* (2013.01)

(58) Field of Classification Search
None
See application file for complete search history.

(56) References Cited

U.S. PATENT DOCUMENTS

| 3,878,565 A | 4/1975 | Sauvage |
| 4,892,539 A | 1/1990 | Koch |
| 9,593,199 B2 * | 3/2017 | Wamprecht ........ C08G 18/4837 |
| 2006/0129234 A1 * | 6/2006 | Phaneuf .................... A61F 2/06 623/1.54 |
| 2016/0302911 A1 | 10/2016 | Soletti |
| 2017/0173226 A1 | 6/2017 | Hai et al. |

FOREIGN PATENT DOCUMENTS

| WO | 2016187698 A1 | 1/2016 |
| WO | 2018053265 A1 | 3/2018 |

OTHER PUBLICATIONS

Zhang et al. Biofabrication 2017 9(2):025010, 1-14 (Year: 2017).*
Bae et al. International Journal of Industrial Entomology 2016 33(2):132-137 (Year: 2016).*
Liu et al. Journal of Materials Chemistry B 2017 5:3758-3764 (Year: 2017).*
Sigma reference—product specification sheet for CAS No. 68084-39-9 (Year: 2011).*
Liu et al. BioMed Central Cardiovascular Disorders 2013 13(70):1-7 (Year: 2013).*
Uttayarat et al. Acta Biomaterialia 2010 6:4229-4237 (Year: 2010).*
Wang et al. Frontiers of Chemical Science and Engineering 2011 5(3):392-400 (Year: 2011).*
Mi et al. Journal of the Mechanical Behavior of Biomedical Materials 2018 78:433-441—available Dec. 1, 2017 (Year: 2018).*
Sankaran et al. Biotechnology Journal 2015 10:96-108 (Year: 2018).*
Zhang et al. Journal of Biomedical Materials Research 2010 93A:984-993 (Year: 2010).*
Yin et al. Colloids and Surfaces B: Biointerfaces 2014 120:47-54 (Year: 2014).*
Uttayarat et al. Journal of Biomedical Materials Research 2005 75A:668-680 (Year: 2005).*
Jiang et al. Langmuir 2002 18: 3273-3280 (Year: 2002).*
Zhang et al. Polymer Composites 2016 37(2):523-531 (Year: 2016).*
Williamson et al. Biomaterials 2006 27:3608-3616 (Year: 2006).*
Khosravi et al. Annals of Biomedical Engineering 2016 44(8):2402-2416 (Year: 2016).*
Ravi et al., Biomaterials for vascular tissue engineering; Regen Med., 2010, vol. 5, No. 1, 21 pages.
Mi et al., Promoting Endothelial Cell Affinity and Antithrombogenicity of Polytetrafluoreothylene (PTFE) by Mussel-Inspired Modification and RGD/Heparin Grafting; J. Mater Chem B; 2018, vol. 6, pp. 3475-3485.
Yu et al., Development of Biomimetic Thermoplastic Polyurethane/Fibroin Small-Diameter Vascular Grafts via a Novel Electrospinning Approach; J. Biomed Mater Res A.; 2018; vol. 106, No. 4. pp. 985-996.

(Continued)

Primary Examiner — Melissa S Mercier
Assistant Examiner — Caralynne E Helm
(74) Attorney, Agent, or Firm — Sandberg Phoenix & von Gontard

(57) ABSTRACT

Disclosed herein are novel wavy, multi-component vascular grafts (WMVGs) with a wavy inner layer of rigid biopolymer fibers and an outer layer of elastic biopolymer fibers and a method for preparing WMVGs via electrospinning using a special assembled collector. The fabricated WMVGs closely mimic the non-linear tensile stress-strain relationship of native blood vessels and showed sufficient mechanical strength needed for implantation.

17 Claims, 15 Drawing Sheets

Specification includes a Sequence Listing.

(56) References Cited

OTHER PUBLICATIONS

Singh, C., Wong, C. S. & Wang, X. Medical Textiles as Vascular Implants and Their Success to Mimic Natural Arteries. J Funct Biomater 6, 500-525, doi:10.3390/jfb6030500 (2015).

* cited by examiner

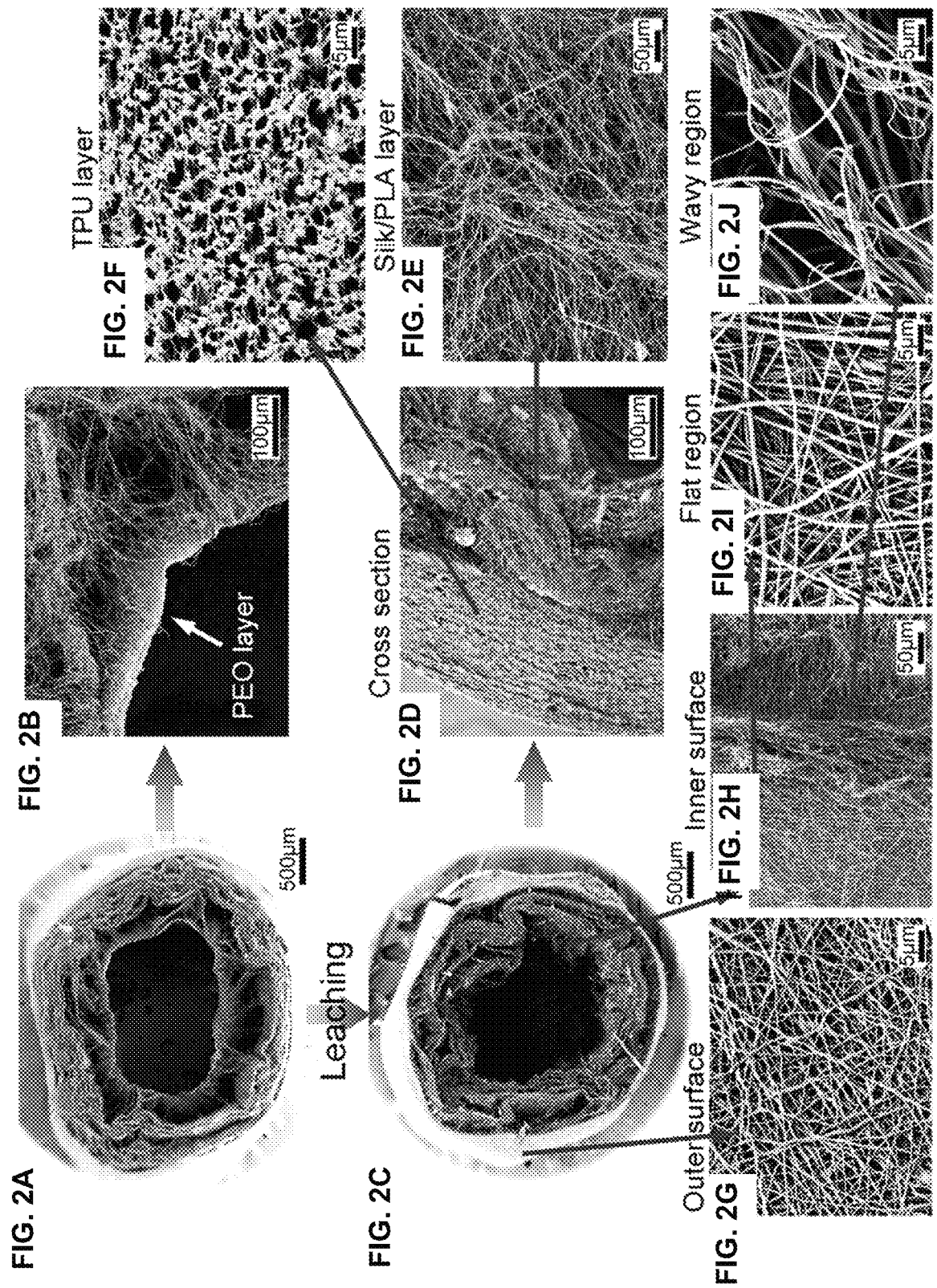

WAVY MULTI-COMPONENT VASCULAR GRAFTS WITH BIOMIMETIC MECHANICAL PROPERTIES, ANTITHROMBOGENICITY, AND ENDOTHELIAL CELL AFFINITY

CROSS REFERENCE TO RELATED APPLICATIONS

This application claims priority to U.S. Provisional Application No. 62/677,931 filed on May 30, 2018, which is hereby incorporated by reference in its entirety.

STATEMENT OF GOVERNMENT SUPPORT

This invention was made with government support under HL134655 awarded by the National Institutes of Health. The government has certain rights in the invention.

INCORPORATION OF SEQUENCE LISTING

A paper copy of the Sequence Listing and a computer readable form of the Sequence Listing containing the file named "P180253_ST25.txt", which is 931 bytes in size (as measured in MICROSOFT WINDOWS® EXPLORER), are provided herein and are herein incorporated by reference. This Sequence Listing consists of SEQ ID NOs:1-4.

BACKGROUND OF THE DISCLOSURE

The present disclosure relates generally to tissue engineering. In particular, the present disclosure relates to artificial vascular grafts that mimic the properties of native blood vessels and can be covered and/or replaced by regenerated tissue depending on the biodegradability of the materials used. The present disclosure is further directed to methods of preparing artificial vascular grafts.

Cardiovascular disease (CVD) is one of the major diseases that threaten human life. Cardiac disorders are usually associated with a blockage of blood vessels. This yields an inadequate nutrient and oxygen supply, thus leading to reduced blood flow and tissue damage. Approximately 400,000 coronary artery and peripheral vascular bypass surgeries are performed each year in the United States. Although synthetic grafts have been successfully used for large-diameter blood vessels, they have, so far, been unsuitable for small diameter (less than 6 mm diameter) blood vessels due to the risk of thrombosis, calcification, and restenosis.

Native blood vessels are composed of three major layers: tunica intima, tunica media, and tunica adventitia. It is believed that the mechanical strength of a blood vessel is mainly provided by the wavy-structured elastin and collagen fibrils. At low pressure conditions, the less wavy elastin was first stretched while collagen fibrils were unfolded and oriented. As the pressure increased, the stiffer collagen fibrils took the primary role in facilitating a steep-increase in strength. This resulted in a unique "toe-region" that gives the blood vessels the ability to withstand repetitive blood pulses while maintaining blood pressure.

The concept of tissue engineering has been successful in large tissues such as skin and bone. Vascular tissue engineering (VTE) involves constructing artificial small diameter vascular grafts (SDVGs) that are capable of mimicking the properties of native blood vessels and that can eventually be replaced by regenerated tissue. To date, many researches have focused on mimicking the multi-layered structure of blood vessels in SDVG fabrication. The clinical application of SDVGs remains elusive since many fabricated SDVGs fail to fully resemble the properties of native blood vessels and meet the requirements for tissue regeneration due to the complex structure and composition of native blood vessels. Although some of them have shown mechanical properties superior to human arteries, they fail to closely resemble the special non-linear stretching response of human blood vessels. Thromboses are another critical challenge for SDVGs, due to the adhesion of platelets on the lumen surface of SDVGs, which results in poor long-term patency. To enhance antithrombogenicity, the incorporation of anti-coagulation chemicals and the introduction of an endothelial cell layer have been attempted. Heparin has been widely used as an anti-coagulation reagent when fabricating SDVGs and for the coating of commercial larger-diameter vascular grafts. However, simply coated heparin molecules tend to gradually release into the bloodstream and are not sustainable for long-term implantation applications. The endothelialization of SDVGs has been difficult since most synthetic materials have a relatively low cell affinity due to their lack of bioactive binding sites. Although human endothelial cells can survive on many synthetic material substrates, they usually exhibit slow proliferation rates and migration speeds.

Vascular grafts made of decellularized extracellular matrices (ECMs) or rolled cell membranes have been highly recognized in recent years because they resemble the native structure and biological configuration of blood vessels. These methods are highly customized, have high cost and variability, and require long cell culture times.

For all of these reasons, SDVGs and methods for preparing SDVGs remain elusive. Accordingly, there exists the need for developing cost-effective SDVGs that can fully mimic the properties of blood vessels, prevent thrombosis, and do not require long maturation times and provide practical treatment of CVDs.

BRIEF DESCRIPTION

Disclosed herein are new wavy, multi-component vascular grafts (WMVGs) composed of hybrid biomaterials with different mechanical properties that resemble the structure and properties of native blood vessels. The WMVG are fabricated by an electrospinning method disclosed in the present disclosure using a custom-designed rotating collector. The resulting WMVG has an inner layer including wavy-structured rigid biopolymer fibers that resemble the properties of collagen in blood vessels and an outer layer including elastic biopolymer fibers that mimic the elastin in blood vessels. During preparation of the WMVG, a first fiber layer of a water soluble polymer is employed as a sacrificial fiber layer that is leached out for easy removal of the resultant electrospun tubular grafts having the rigid biopolymer fiber inner layer and the elastic biopolymer fiber outer layer from the rotating collector. Advantageously, because of the wavy fibrous structure of the inner layer and the material combination, the WMVGs of the present disclosure exhibit the unique non-linear tensile stress-strain behavior of human arteries. The WMVGs of the present disclosure also advantageously prevent thrombosis and can be covered and/or replaced by regenerated tissue, depending on the biodegradability of the materials used.

Moreover, surface modification of the WMVGs can be used to enhance the biocompatibility of the inner surface of the wavy-structured rigid biopolymer fibers. In particular, biomolecules can be coated on the wavy-structured rigid biopolymer fibers in an aqueous solution through simple grafting methods based on mussel-inspired chemistry. The modified wavy-structured rigid biopolymer fibers advantageously have a significantly increased cell proliferation and migration rate, as well as increased cell-substrate interactions. The addition of biomolecules also contributes to the dramatically enhanced antithrombogenicity. Along with the enhanced endothelialization on their inner surfaces, the biomimetic WMVGs fabricated provide candidates for CVD treatment.

In one aspect, the present disclosure is directed to a wavy multi-component vascular graft comprising an inner layer comprising rigid biopolymer fibers and an outer layer comprising thermoplastic polyurethane (TPU) fibers.

In one aspect, the present disclosure is directed to a method for preparing a wavy multi-component vascular graft. The method includes: electrospinning a first solution comprising a water soluble polymer material to form a first water soluble fiber; collecting the first water soluble fiber on an assembled mandrel that comprises a central tube and a plurality of satellite cylinders surrounding the tube to form a first water soluble fiber layer; electrospinning a second solution comprising a rigid biopolymer material to form a second fiber; collecting the second fibers on the first water soluble fiber layer to form a rigid biopolymer fiber layer; electrospinning a third solution comprising an elastic polymer material to form a third fiber; collecting the third fibers on the rigid biopolymer fiber layer on the assembled mandrel to form an outer elastic polymer fiber layer; and removing the assembled mandrel to form a wavy multi-component vascular graft.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIGS. 2A-2J are electron micrographs depicting the microstructure of WMVGs. FIG. 2A depicts a low magnification cross-sectional image of a WMVG removed from the mandrel before poly(ethylene oxide) (PEO) leaching. FIG. 2B depicts a high magnification cross-sectional image of a WMVG removed from the mandrel before PEO leaching. FIG. 2C depicts a low magnification cross-sectional image of a WMVG removed from the mandrel after PEO leaching. FIG. 2D depicts a high magnification cross-sectional image of a WMVG removed from the mandrel after PEO leaching. FIGS. 2E and 2F depict cross-sectional images of the silk/poly(lactic acid) (PLA) inner fiber layer (FIG. 2E) and the TPU outer fiber layer (FIG. 2F). FIGS. 2G and 2H depict the structure of the outer surface (FIG. 2G) and the inner surface (FIG. 2H) of a WMVG. FIGS. 2I and 2J depict enlarged images of the flat region (FIG. 2I) and wavy region (FIG. 2J) of the inner surface of a WMVG.

FIG. 3A depicts representative tensile test curves for S/P:T=1:2 (S/P: silk/PLA, T:TPU, 1:2 solution blend ratio), S/P:T=1:1, and S/P:T=2:1 vascular grafts. FIG. 3B depicts suture retention results for S/P:T=1:2, S/P:T=1:1, and S/P:T=2:1 vascular grafts. FIG. 3C depicts burst pressure results for S/P:T=1:2, S/P:T=1:1, and S/P:T=2:1 vascular grafts. FIG. 3D depicts cyclic tensile test results of S/P:T=1:2. FIG. 3E depicts cyclic tensile test results of S/P:T=1:1. FIG. 3F depicts cyclic tensile test results of S/P:T=2:1 vascular grafts. FIG. 3G is a schematic illustration depicting the WMVG's cyclic circumferential expansion behavior mimicking native blood vessels.

FIG. 4A depicts a low resolution SEM image of S/P fiber mat; FIG. 4B depicts a high resolution SEM image of S/P fiber mat; FIG. 4C depicts XPS survey scans of S/P fiber mat; FIG. 4D depicts a low resolution SEM of S/P-DA fiber mat; FIG. 4E depicts a high resolution SEM of S/P-DA fiber mat; FIG. 4F depicts XPS survey scans of S/P-DA fiber mat; FIG. 4G depicts a low resolution SEM of SIP-D&H fiber mat; FIG. 4H depicts a high resolution SEM of SIP-D&H fiber mat; FIG. 4I depicts XPS survey scans of SIP-D&H fiber mat.

FIG. 5A depicts water contact angle results of different S/P fiber mats. FIG. 5B depicts platelet attachment test results. FIG. 5C depicts representative SEM image of S/P fiber mats; FIG. 5D depicts representative SEM image of S/P-DA fiber mats, and FIG. 5E depicts representative SEM image of SIP-D&H fiber mats.

FIG. 6A depicts fluorescence images from the live/dead assay of human umbilical vein endothelial cell (HUVECs) cultured on differently modified S/P substrates. FIG. 6B depicts cell proliferation statistical results from the MTS assay. FIG. 6C depicts cell viability statistical results.

FIG. 11A shows the average projected cell area. FIG. 11B shows the average cell aspect ratio.

DETAILED DESCRIPTION

Figure 1:
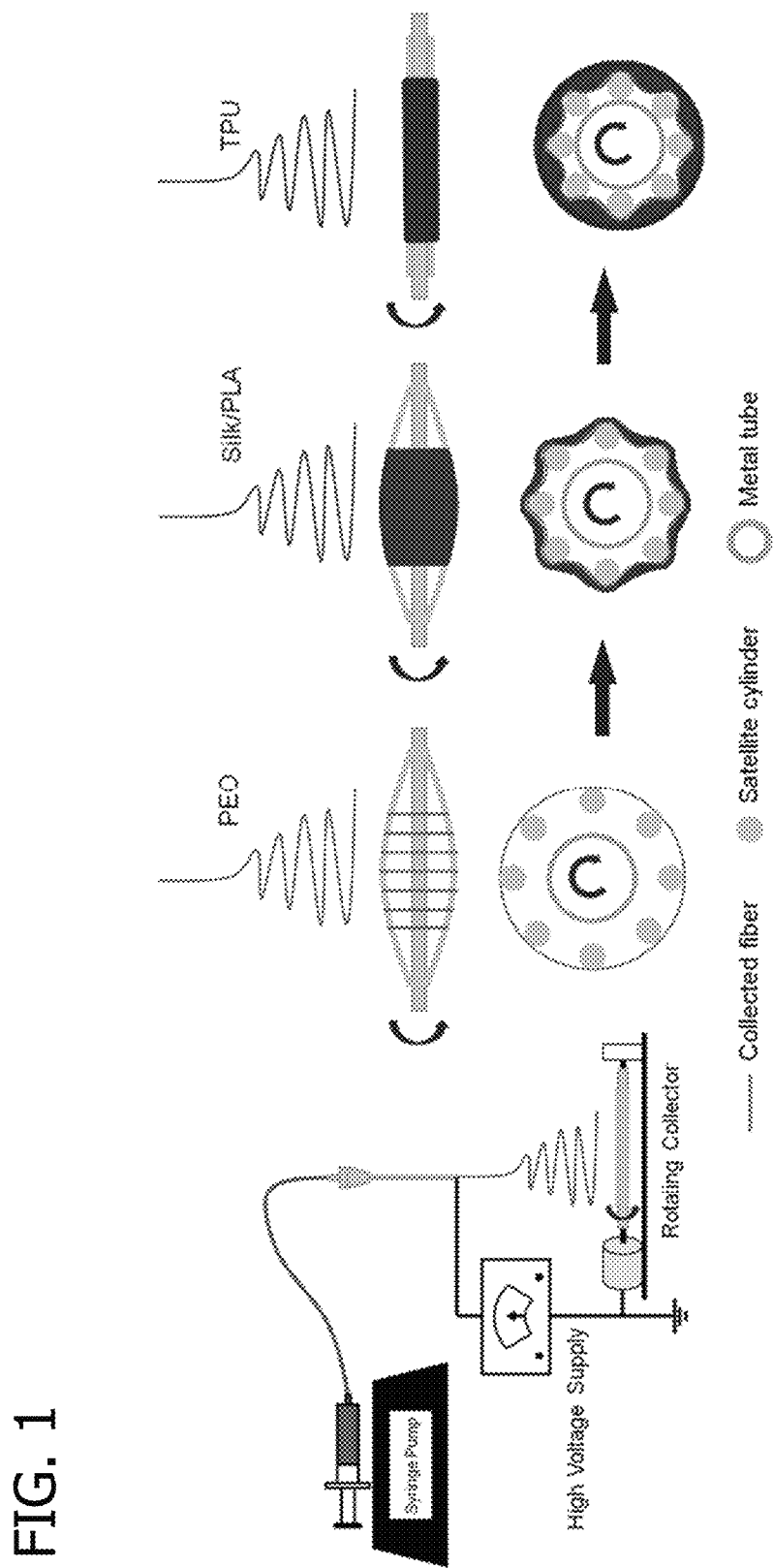
FIG. 1 is a schematic depicting the fabrication procedure for wavy multi-component vascular grafts (WMVGs) using a custom-designed rotating collector.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

As used herein, "wavy multi-component vascular graft" refers to a vascular graft which, when viewed in cross-section, presents a wavy inner fiber layer morphology and includes at least two biocompatible polymers having different stiffness. As used herein, "wavy" refers to a surface having a series of undulating and wavelike curves. Thus, the inner layer of the wavy vascular grafts of the present disclosure has a series of undulating and wavelike curves when the vascular grafts are viewed in cross-section (see, for example, FIG. 2C).

As used herein, "small-diameter vascular graft" refers to a vascular graft having a lumen diameter less than 6 mm. Vascular graft is a engineered tubular graft that is intended to replace or bypass a damaged or occluded blood vessel.

Wavy Multi-Component Vascular Grafts

In one aspect, the present disclosure is directed to a wavy multi-component vascular graft comprising an inner fiber layer comprising rigid biopolymer fibers and an outer fiber layer comprising elastic biopolymer fibers.

Suitable polymer materials for preparing the inner rigid biopolymer fiber layer include silk, poly(lactic acid) (PLA), poly(L-lactic acid) (PLLA), polycaprolactone (PCL), polylactic-co-glycolic acid (PLGA), poly(glycolic acid) (PGA), PLLA/PLGA copolymer, collagen, chitosan, alginate, and combinations thereof. Particularly suitable rigid biopolymers for the rigid biopolymer fibers is silk/poly(lactic acid) fibers. The rigid fibers include submicron diameter fibers. The rigid fibers comprise an average fiber diameter ranging from about 100 nm to about 1000 nm.

Suitable polymer materials for preparing the outer elastic biopolymer fiber layer include thermoplastic polyurethane (TPU), polyglycerol sebacate (PGS), poly(ester urethane) urea (PEUU), and combinations thereof. The elastic fibers include nanoscale diameter fibers and submicron diameter fibers. Suitably, elastic biopolymers fibers include an average fiber diameter ranging from about 50 nm to about 300 nm.

The wavy multi-component vascular graft can further include a biomolecule. Suitable biomolecules include dopamine, heparin, cell adhesion molecules, growth factors, chemokines, anticoagulants, and combinations thereof. Suitable cell adhesion molecules include fibronectin, arginine-glycine-aspartic acid (RGD) peptide, arginine-glycine-aspartic acid-serine (RGDS) peptide (SEQ ID NO:1), leucine-aspartic acid-valine (LDV) peptide, fibronectin CS1 region, laminin, tyrosine-isoleucine-glycine-serine-arginine (YIGSR) peptide (SEQ ID NO:2), proline-aspartic acid-serine-glycine-arginine (PDSGR) peptide (SEQ ID NO:3), lysine-arginine-glutamic acid (LRE) peptide, vitronectin, arginine-glycine-aspartic acid-valine (RGDV) peptide (SEQ ID NO:4), and combinations thereof. Suitable anticoagulants include heparin, low molecular weight heparin, a coumarin, a directly acting oral anticoagulants (DOACs), fondaparinux, idraparinux, a factor Xa inhibitor, a thrombin inhibitor, hementin, and combinations thereof. Suitable coumarins include warfarin, acenocoumarol, phenprocoumon, atromentin, and phenindione. Suitable directly acting oral anticoagulants (DOACs) include dabigatran, rivaroxaban, apixaban, edoxaban and betrixaban. Suitable factor Xa inhibitors include rivaroxaban, apixaban, edoxaban, betrixaban, darexaban, letaxaban, and eribaxaban. Suitable thrombin inhibitors include hirudin, lepirudin, bivalirudin, argatroban, dabigatran, ximelagatran and combinations thereof. Suitable growth factors include, for example, fibroblast growth factor, vascular endothelial growth factor, transforming growth factor beta, and combinations thereof. Suitable chemokines include, for example, SDF-1α, CD47, and combinations thereof.

The wavy multi-component vascular graft can further include a cell. Suitable cells include endothelial cells, smooth muscle cells, mesenchymal stem cells, umbilical vein endothelial cells, fibroblast cells, and combinations thereof. The seeded cells can then be cultured for a sufficient period of time for cells to migrate, proliferate and differentiate.

The wavy multi-component vascular graft can include a lumen diameter ranging from about 1.9 mm to about 2.3 mm. The lumen diameter can be made larger by using a larger diameter mandrel. The lumen diameter can be made smaller by using a smaller diameter mandrel.

The wall thickness of the wavy multi-component vascular graft can be any desirable thickness. Suitable wall thickness can range from about 200 µm to about 500 µm. The wall thickness can be determined by measuring from the inner layer surface facing the lumen to the outermost surface of the wavy multi-component vascular graft of cross-sectional scanning electron micrograph images. The wall thickness of the wavy multi-component vascular graft can be made thicker by depositing more of the rigid biopolymer fibers (to result in a thicker inner fiber layer), by depositing more of the elastic biopolymer fibers (to result in a thicker outer fiber layer), and combinations thereof (to result in a thicker inner fiber layer and a thicker outer fiber layer). The wall thickness of the wavy multi-component vascular graft can be made thinner by depositing less of the rigid biopolymer fibers (to result in a thinner inner fiber layer), by depositing less of the elastic biopolymer fibers (to result in a thinner outer fiber layer), and combinations thereof (to result in a thinner inner fiber layer and a thinner outer fiber layer).

The wavy multi-component vascular graft can include a suture retention strength ranging from about 1 Newton (N) to about 4 N. Suture retention strength can be by varying the contents of rigid fiber layer and the elastic fiber layer.

The wavy multi-component vascular graft can include any desired burst pressure. The burst pressure can be increased by increasing the TPU fiber content. Suitable burst pressures range from about from 800 mmHg to about 1800 mmHg.

The tensile strength and modulus of WMVGs can be increased by increasing the silk/PLA fiber content. The flexibility of WMVGs can be increased by increasing the TPU fiber content. The elongation-at-break of WMVGs can be increased by increasing the TPU fiber content.

Because of the porous structure, and if biodegradable material components are used, the WMVGs can gradually degrade be replaced by regenerated native blood vessel tissue. The degradation rate of WMVGs can be controlled by selecting biopolymers with different degradation rates. For the silk/PLA and TPU based WMVG, silk and PLA fibers should degrade within 6 months, while the TPU fibers could be maintained for about two years. Generally, the inner fiber layer desirably degrades within about 6 months, while the outer fiber layer is maintained for about 2 years.

Method for Preparing a Wavy Multi-Component Vascular Graft

In one aspect, the present disclosure is directed to a method for preparing a wavy multi-component vascular graft. The method includes: electrospinning a first solution comprising a water soluble polymer material to form a first water soluble fiber; collecting the first water soluble fiber on an assembled mandrel that comprises a central tube and a plurality of satellite cylinders surrounding the tube to form a first water soluble fiber layer; electrospinning a second solution comprising a rigid biopolymer material to form a second fiber; collecting the second fibers on the first water soluble fiber layer to form an inner rigid biopolymer fiber layer; electrospinning a third solution comprising an elastic biopolymer material to form a third fiber; collecting the third fibers on the rigid biopolymer fiber layer on the assembled mandrel to form an outer elastic biopolymer fiber layer; and removing the assembled mandrel to form a wavy multi-component vascular graft.

As used herein, "electrospinning" or "electrospun," refers to any method where materials are streamed, sprayed, sputtered, dripped, or otherwise transported in the presence of an electric field. As known to those skilled in the art, electrospinning generally involves the creation of an electrical field at the surface of a liquid. The resulting electrical forces create a jet of liquid which carries electrical charge. The electrically charged solution is then streamed through an opening or orifice towards a grounded target. As the jet of liquid elongates and travels, it will harden and dry to produce fibers. According to the method of the present disclosure, electrospun material is deposited from the direction of a charged container towards a grounded target (to the assembled mandrel), or from a grounded container in the direction of a charged target (to the assembled mandrel).

The water soluble polymer material of the first solution, the rigid biopolymer material of the second solution, and the elastic polymer material of the third solution can be dissolved or suspended in a solution or suspension of water, urea, methanol, chloroform, monochloroacetic acid, isopropanol, 2,2,2-trifluoroethanol, 1,1,1,3,3,3-hexafluoro-2-propanol (also known as hexafluoroisopropanol or HFP), acetamide, N-methylformamide, N,N-dimethylformamide (DMF), dimethylsulfoxide (DMSO), dimethylacetamide, N-methyl pyrrolidone (NMP), acetic acid, trifluoroacetic acid, ethyl acetate, acetonitrile, trifluoroacetic anhydride, 1,1,1-trifluoroacetone, maleic acid, hexafluoroacetone, and combinations thereof.

Any water soluble polymer material that can be electrospun can be used to form the first water soluble fiber. Suitable water soluble polymer materials include poly(ethylene oxide) (PEO) and poly vinyl alcohol (PVOH). The method can further include removing the first water soluble fiber layer. Suitably, the first water soluble fiber layer can be removed by soaking the grafts in water, saline, and other solutions. The first water soluble fiber layer can also be removed by flowing water, saline, and other solutions through the lumen of the grafts.

Suitable polymer materials for preparing the inner rigid biopolymer fiber layer include silk, poly(lactic acid) (PLA), poly(L-lactic acid) (PLLA), polycaprolactone (PCL), poly-lactic-co-glycolic acid (PLGA), poly(glycolic acid) (PGA), PLLA/PLGA copolymer, collagen, chitosan, alginate, and combinations thereof. Particularly suitable rigid biopolymers for the rigid biopolymer fibers is silk/poly(lactic acid) fibers. The rigid fibers include submicron diameter fibers. The rigid fibers comprise an average fiber diameter ranging from about 100 nm to about 1000 nm.

Suitable polymer materials for preparing the outer elastic biopolymer fiber layer include thermoplastic polyurethane (TPU), polyglycerol sebacate (PGS), poly(ester urethane) urea (PEUU), and combinations thereof. The elastic fibers include nanoscale diameter fibers and submicron diameter fibers. Suitably, elastic biopolymers fibers include an average fiber diameter average fiber diameter ranging from about 50 nm to about 300 nm.

Suitably, a volume ratio of the rigid biopolymer solution to the elastic biopolymer solution can range from about 1:2 to about 2:1.

Suitable polymer materials for preparing the outer elastic biopolymer fiber layer include thermoplastic polyurethane (TPU), polyglycerol sebacate (PGS), poly(ester urethane) urea (PEUU), and combinations thereof. The elastic fibers include nanoscale diameter fibers and submicron diameter fibers. Suitably, elastic biopolymers fibers include an average fiber diameter average fiber diameter ranging from about 50 nm to about 300 nm.

The resultant wavy multi-component vascular graft prepared according to the method includes a wavy inner layer of rigid biopolymer fibers and a smooth outer layer of elastic biopolymer fibers.

The method can further include modifying the inner layer of rigid biopolymer fibers. The inner layer of rigid biopolymer fiber layer can be modified with a biomolecule. Suitable biomolecules include dopamine, heparin, cell adhesion molecules, growth factors, chemokines, anticoagulants, and combinations thereof. Suitable biomolecules include dopamine, heparin, cell adhesion molecules, growth factors, chemokines, anticoagulants, and combinations thereof. Suitable cell adhesion molecules include fibronectin, arginine-glycine-aspartic acid (RGD) peptide, arginine-glycine-aspartic acid-serine (RGDS) peptide (SEQ ID NO:1), leucine-aspartic acid-valine (LDV) peptide, fibronectin CS1 region, laminin, tyrosine-isoleucine-glycine-serine-arginine (YIGSR) peptide (SEQ ID NO:2), proline-aspartic acid-serine-glycine-arginine (PDSGR) peptide (SEQ ID NO:3), lysine-arginine-glutamic acid (LRE) peptide, vitronectin, arginine-glycine-aspartic acid-valine (RGDV) peptide (SEQ ID NO:4), and combinations thereof. Suitable anticoagulants include heparin, low molecular weight heparin, a coumarin, a directly acting oral anticoagulants (DOACs), fondaparinux, idraparinux, a factor Xa inhibitor, a thrombin inhibitor, hementin, and combinations thereof. Suitable coumarins include warfarin, acenocoumarol, phenprocoumon, atromentin, and phenindione. Suitable directly acting oral anticoagulants (DOACs) include dabigatran, rivaroxaban, apixaban, edoxaban and betrixaban. Suitable factor Xa inhibitors include rivaroxaban, apixaban, edoxaban, betrixaban, darexaban, letaxaban, and eribaxaban. Suitable thrombin inhibitors include hirudin, lepirudin, bivalirudin, argatroban, dabigatran, ximelagatran and combinations thereof. Suitable growth factors include, for example, fibroblast growth factor, vascular endothelial growth factor, transforming growth factor beta, and combinations thereof. Suitable chemokines include, for example, SDF-1α, CD47, and combinations thereof. The inner layer of rigid biopolymer fibers can be modified by immersing the WMVG in a solution containing the biomolecule.

The method can further include seeding a cell on the wavy multi-component vascular graft. Suitable cells include endothelial cells, smooth muscle cells, mesenchymal stem cells, fibroblasts, and combinations thereof. Cells are suitably seeded by injecting a cell suspension into the lumen of the WMVG followed by adding cell culture media. The seeded WMVG can then be cultured for a sufficient period of time for cells to migrate, proliferate, and differentiate.

Various functions and advantages of these and other embodiments of the present disclosure will be more fully understood from the examples shown below. The examples are intended to illustrate the benefits of the present disclosure, but do not exemplify the full scope of the disclosure.

EXAMPLES

Materials and Methods

Poly(lactic acid) (PLA, $M_w$: ~60,000) and poly(ethylene oxide) (PEO, $M_v$: ~900,00) were purchased from Sigma-Aldrich. Hexafluoroisopropanol (HFIP) was purchased from CovaChem. Biodegradable elastic thermoplastic polyurethane (TPU) with a molecular weight of 80,000 was synthesized. Silk fibroin was extracted from the cocoons of

*Bombyx mori* silkworms. All other chemicals and solvents were purchased from Sigma-Aldrich. Milli-Q DI water was used throughout the experiment.

The PEO solution was prepared by dissolving 1 g of PEO powder in deionized (DI) water at 50° C. The silk/PLA solution was prepared by dissolving 200 mg PLA and 240 mg silk fibroin in 5 mL HFIP at room temperature. The TPU solution was prepared by dissolving 1 g TPU pellets in 10 mL DMF at 60° C. All solutions were magnetically stirred overnight and used as prepared.

Fabrication of Wavy Multi-Component Vascular Grafts (WMVGs)

WMVGs were fabricated via electrospinning using a special rotating fiber collection device. The device used an assembled mandrel having a central tube and eight satellite cylinders surrounding the tube. In the fabrication process, as shown in FIG. 1, the satellite cylinders expand (jump rope effect) when the mandrel starts rotating and electrospun fibers are thus loosely collected on the mandrel. A thin PEO layer was first electrospun on the mandrel, followed by electrospinning of the silk/PLA layer and the TPU layer. As the collected graft thickened, the expansion of the satellite cylinders decreased due to increasing wrapping force from the electrospun fibers. The electrospinning of elastic TPU fibers eventually tighten the graft and mandrel. The electrospun assembly was first treated with methanol vapor overnight to make silk fibroin water insoluble. Afterwards, the inner PEO layer was removed by leaching in a water bath for 2 hours so that the vascular graft sample could be removed. At the end, a vascular graft with a wavy inner layer of silk/PLA fibers and a smooth TPU nanofiber outer layer was prepared. The electrospinning volumes of the silk/PLA solution and the TPU solution were kept at 0.5 mL and 1 mL, 0.75 mL and 0.75 mL, and 1 mL and 0.5 mL, respectively, to alter the blend ratio and thus the mechanical properties of the vascular grafts. The samples were denoted as S/P:T=1:2, S/P:T=1:1, and S/P:T=2:1.

Characterization of WMVGs

The morphology of WMVGs was imaged using a digital LEO GEMINI 1530 scanning electron microscope (SEM, Zeiss). Samples were quenched in liquid nitrogen, fractured, and sputtered with a thin film of gold for 40 seconds prior to imaging with an accelerating voltage of 3 kV. The fiber diameters were measured from SEM images using Image Pro-plus software. At least 50 fibers were measured for each sample.

The mechanical properties of the WMVGs were characterized via a universal mechanical property testing instrument (Instron). The tensile properties of the WMVGs were measured in the circumferential direction via two "U"-shaped clamps. Samples were stretched circumferentially at a crosshead speed of 1 mm/min until fracture. Cyclic tensile tests were also performed using the same instrument. All samples were stretched to 30% strain and released for 50 cycles at a crosshead speed of 5 mm/min.

The suture retention strengths of the WMVGs were measured on samples with a length of 20 mm. One end of the sample was clamped by a fixed clamp, while the other end was pierced through at 2 mm from the edge using a tapered non-cutting needle connected to a movable clamp by a commercial suture (5-0 prolene suture, Ethicon, Inc.). Samples were stretched at 5 mm/min until fractured. The maximum load was recorded as the suture retention strength.

The burst pressure of WMVGs was measured using a custom-made apparatus consisting of a digital pump, a pressure gage, and a sample holder. A syringe loaded with a phosphate buffered saline (PBS) was connected to a pressure gage which is then connected to one end of the sample. The PBS was continuously injected into the sample and the other end of the sample was sealed by a clamp once PBS started to flow out. The PBS continued to be injected into the sample until it leaked, and the maximum pressure was recorded as the burst pressure.

Modification on the Inner Surface of WMVGs

Dopamine (DA), a mussel adhesive protein-inspired molecule and an important organic chemical that is found in the human brain and body, was first coated on the electrospun silk/PLA fibers to enhance their biocompatibility and endothelial cell affinity while promoting immobilization of heparin. Briefly, silk/PLA fiber mats were cleaned in 20% ethanol followed by several DI water rinses and drying. Samples were then immersed in a 2 mg/mL dopamine solution with a pH of 8.5 adjusted by 10 mM tris(hydroxymethyl)aminomethane for 16 hours at room temperature. After coating, samples were rinsed with DI water 5 times and dried with nitrogen. The obtained samples were named S/P-DA.

Heparin was coated on the S/P-DA to enhance the antithrombogenicity of WMVGs. Briefly, heparin was dissolved in a citric acid/sodium phosphate dibasic buffer solution with a pH of 5.0 at a concentration of 1 mg/mL. S/P-DA was immersed in the heparin solution for 12 hours at room temperature, followed by several rinsing and drying cycles. The obtained samples were named S/P-D&H.

Characterization of Modified Silk/PLA Fiber Mats

The morphology of the modified silk/PLA fibers was imaged using the same SEM. The surface chemistry was evaluated using an X-ray photoelectron spectrometer (XPS) with a focused, monochromatic K-alpha X-ray source and a monoatomic/cluster ion gun (Thermo Scientific). Water contact angle (WCA) measurements were performed at room temperature with a Dataphysics OCA 15 optical contact angle measuring system using the sessile drop method.

Platelet Adhesion

Platelet adhesion tests were performed to investigate the antithrombogenicity of the as-spun silk/PLA fibers and modified S/P-DA and S/P-D&H samples. Platelet-rich plasma (PRP) was extracted from fresh human blood stabilized with 3.8% sodium citrate as an anti-coagulant (Innovative Research). The blood was centrifuged at 1500 rpm for 15 minutes to obtain PRP. For the platelet adhesion test, samples were first incubated in PBS at 37° C. for 1 hour. Then, PBS was aspirated and 500 µL of PRP were added, followed by incubation at 37° C. for 2 hour. After incubation, samples were rinsed three times with PBS and treated with 2.5 wt % glutaraldehyde in PBS at 4° C. for 1 day. After that, samples were subjected to a series of ethanol solution washes (50%, 70%, 80%, 90%, and 100%) and dried in a desiccator overnight, followed by gold coating and imaging using SEM.

Human Umbilical Vein Endothelial Cell (HUVEC) Culture

HUVECs (Lonza) were maintained on T75 tissue culture-treated polystyrene flasks. The cells were fed every other day with an endothelial cell growth medium EGM-2-MV bullet kit (Lonza). As-spun silk/PLA and modified silk/PLA samples were punched to the same size, placed in 24-well tissue culture plates, and washed in a 20% ethanol solution five times, followed by washing with PBS three times. They were then sterilized with ultraviolet (UV) light for 30 min. HUVECs were detached enzymatically with a trypsin-EDTA solution and seeded on the samples at a density of $1 \times 10^4$ cells/cm$^2$ for the live/dead assay and the MTS assay. They were also seeded at a density of $1 \times 10^3$ cells/cm$^2$ for the cytoskeleton assay. Spent medium was aspirated and replaced with 1 mL of fresh medium daily for screening samples. HUVECs were also cultured on glass slides as a control group for the MTS assay.

HUVECs were also seeded on dopamine- and heparin-modified WMVGs to investigate cell proliferation. For the seeding process, WMVG with a length of 5 mm were sterilized and fixed in a 96-well plate with sterilized polyester double-sided adhesive tape (ARCARE®90106, Adhesive Research Inc.). HUVEC suspensions were concentrated to $2\times10^5$ cells/mL and 50 µL cell suspensions were injected into the lumen of the WMVG, followed by adding 250 µL of cell culture media. Samples were investigated via live/dead assay on day 7 and day 14.

Live/Dead Assay

Cell viability was assessed via a Live/Dead viability/cytotoxicity kit (Life Technologies). The staining protocol followed the manufacturer's instructions. The green fluorescent calcein-AM was used to target the living cells, while the red fluorescence ethidium homodimer-1 (EthD-1) was used to indicate cell death. Stained cells were imaged with a Nikon Ti-E confocal microscope. Nis-D Elements Advanced Research v.3.22 software was used for image analysis.

MTS Assay

Cell proliferation was evaluated using an MTS assay after culturing for 3, 7, and 14 days using a CellTiter 96 Aqueous One Solution kit following the manufacturer's instructions (Promega Life Sciences). Upon testing, cells were treated with media containing a 20% MTS solution and incubated for 1 hour. Then, 100 µL of spent media were transferred into a clear 96-well plate. The absorbance of the plates at a wavelength of 450 nm was read with a Glomax-Multi+ Multiplate Reader (Promega). The subsequent number of cells was determined relative to the negative control.

Cell Cytoskeleton and Morphology

The shape and cytoskeleton organization of the cells were determined by phalloidin-tetramethylrhodamine B isothiocyanate (phalloidin-TMRho, Sigma) staining. For this assay, cells were first fixed in 4% paraformaldehyde and then diluted in PBS for 15 minutes at room temperature. Next, they were washed with PBS and permeabilized with 0.1% Triton-X in PBS for 5 minutes. The cells were then washed once again and treated with 0.3 µM of phalloidin-TMRho with 4', 6-diamidino-2-phenylindole (DAPI) for 1 hour at room temperature. Samples were then washed with PBS and imaged using a Nikon A1RSi inverted confocal microscope. After imaging, the cells were dehydrated using a series of ethanol solution washes (50%, 70%, 80%, 90%, and 100%) and dried in a desiccator overnight followed by gold coating and imaging using SEM.

Statistical Analysis

All biological results are presented as the mean±the standard deviation. All of the values were averaged at least in triplicate and expressed as the mean±the standard deviation. The data were analyzed using the one-way analysis of variance method (ANOVA). Tukey's test was then used to evaluate the specific differences of the data, and these differences were considered statistically significant at $p<0.05$.

FIG. 2A shows the cross-section morphology of the WMVG sample (S/P:T=1:1) removed from the mandrel without leaching of PEO. The inner layer was deformed when pulled out of the satellite cylinders. The PEO layer, which was still attached to the silk/PLA fibers, was clearly observed in the enlarged image (FIG. 2B). The wavy configuration of the inner silk/PLA layer was maintained with the leaching process (FIG. 2C). The enlarged images (FIGS. 2D-2F) show the cross section of the silk/PLA layer and the TPU layer.

Figure 9A:
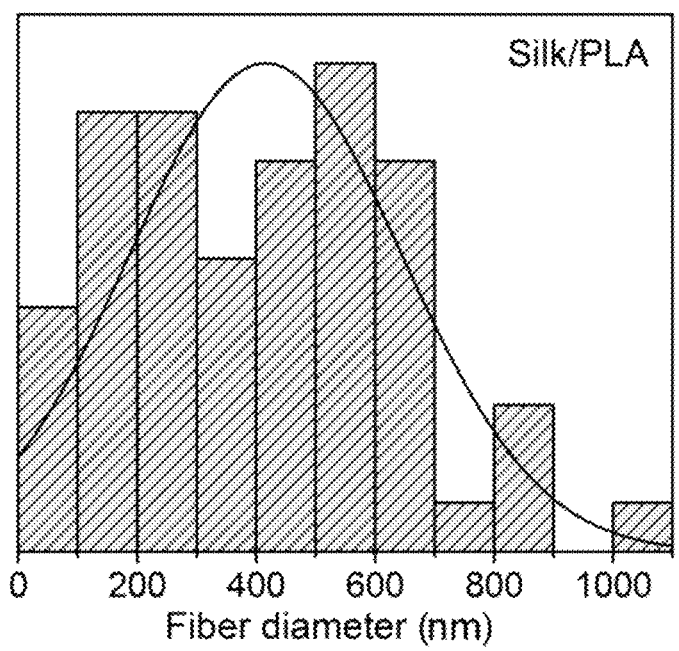
FIGS. 9A and 9B (=S1) depict fiber diameter distribution from the silk/PLA inner fiber layer (FIG. 9A) and the TPU outer fiber layer (FIG. 9B).
Figure 9B:
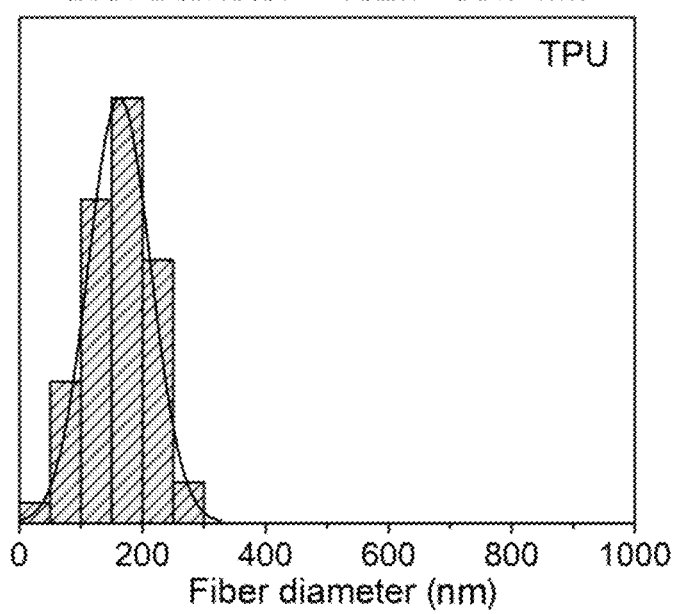
Figure 10A:
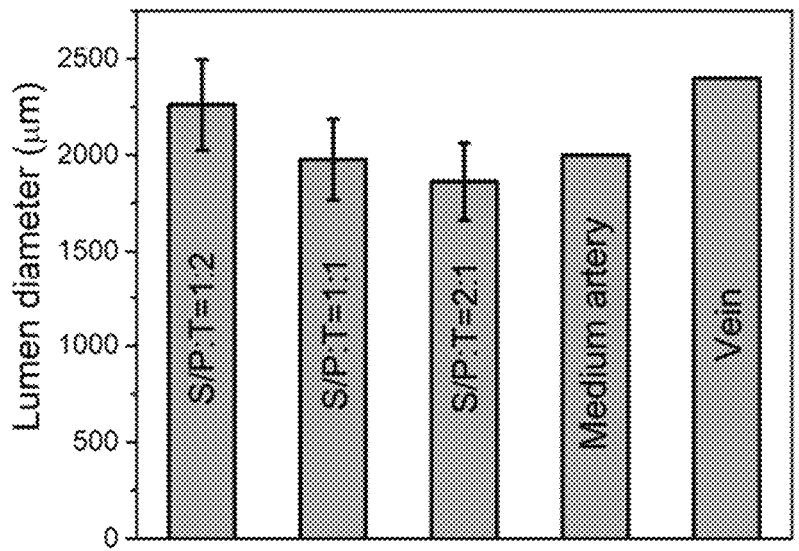
FIGS. 10A and 10B (=S2) depict measurement results of the lumen diameter (FIG. 10A) and the wall thickness of fabricated WDVGs compared to a medium-size human artery and human vein.
Figure 10B:
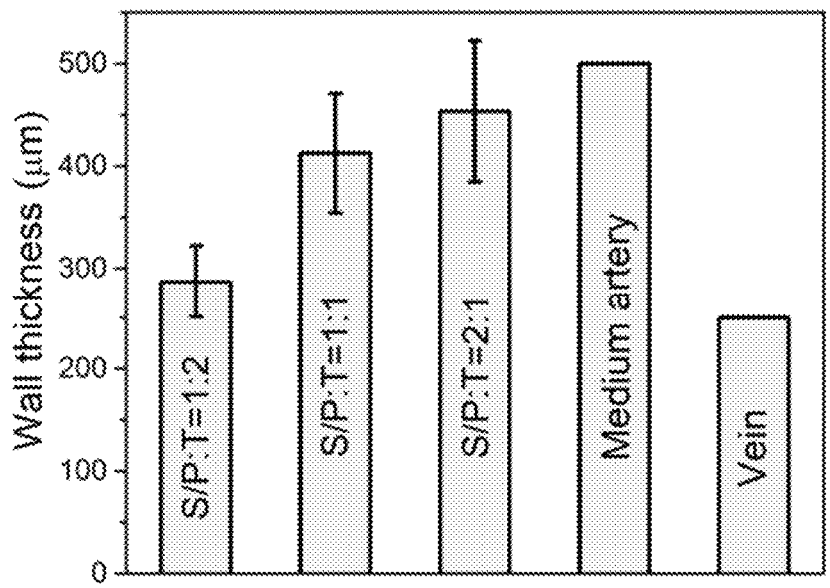

The fabricated WMVGs featured a wavy inner layer made of silk/PLA microfibers and a smooth TPU nanofiber outer layer. The statistical results indicated that the silk/PLA layer was mainly composed of submicron fibers, with an average fiber diameter of 416 nm (see, FIG. 9A). The TPU layer was composed of nano- and submicron fibers, with an average fiber diameter of 163 nm (FIG. 9B). It was also found that the TPU fibers were densely stacked (FIG. 2F), while the silk/PLA fibers were loosely packed due to the electrostatic charge of silk (FIG. 2E). WMVGs with different volumetric blend ratios (i.e., S/P:T=1:2, S/P:T=1:1, and S/P:T=2:1) showed slightly different overall dimensions even though the same total electrospinning volume was used (FIGS. 10A and 10B). The WMVGs possessed smooth outer surfaces (FIG. 2G) and wavy-structured inner surfaces (FIG. 2H). The flat regions of the inner surface (FIG. 2I) were composed of fibers that were in contact with the satellite cylinders of the mandrel and the wavy regions of the inner surface (FIG. 2J) were the fibers located between the satellite cylinders. As prepared for these Examples, WMVGs had a lumen diameter ranging from 1.9 mm to 2.3 mm and a wall thickness ranging from 286 µm to 453 µm. The lumen diameter (FIG. 10A) and wall thickness (FIG. 10B) of fabricated WMVGs were comparable to a medium-size human artery and a human vein.

Figure 3A:
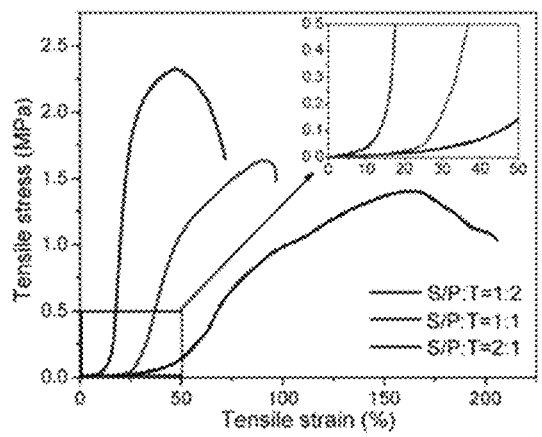
FIGS. 3A-3G depict the mechanical properties of WMVGs.

FIG. 3A shows the tensile stress-strain curves of three WMVGs. The tensile strength and modulus were higher for the WMVGs with more silk/PLA microfibers since both silk and PLA are relatively more rigid and stronger. As the TPU content was increased, the WMVGs became more flexible as indicated by their reduced strength and modulus as well as increased elongation-at-break (Table 1). Advantageously, unlike many synthetic materials, all WMVGs showed an initial slow increase of stress at low strain and a steep increase of stress at high strain, which resembled the "toe region" of native blood vessels. The statistical results also showed that the tensile strength of WMVGs surpassed native human arteries, and that the toe regions were within the range (9-38%) of human coronary arteries (cf. Table 1).

TABLE 1

Statistical results of the mechanical properties of fabricated WDVGs compared to referenced natural arteries.

| WDVGS | Modulus (MPa) | Strength (MPa) | Elongation-at-Break (%) | Toe Region (%) |
|---|---|---|---|---|
| S/P:T = 1:2 | 2.46 | 1.42 | 203.5 | 34.5 |
| S/P:T = 1:1 | 5.66 | 1.63 | 97.5 | 22.3 |
| S/P:T = 2:1 | 22.5 | 2.33 | 70.8 | 10.1 |
| Coronary artery | 1.42 | 0.10 | 34.2 | 9~38% |
| Internal mammary artery | 1.18 | 0.10 | 35.1 | / |
| Porcine coronary artery | 1.50 | 2.40 | 105.2 | / |

Figure 3B:
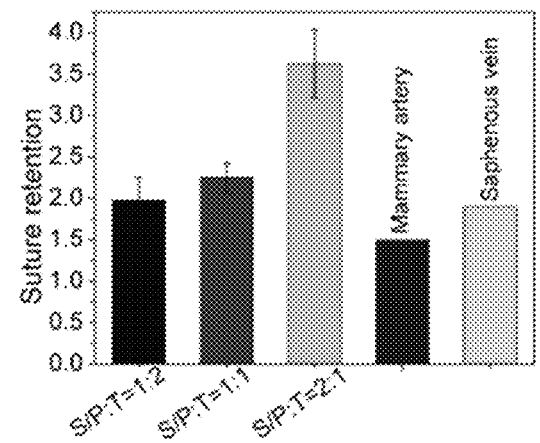

The suture retention strength was measured to verify the applicability of WMVGs for transplant surgery. As shown in FIG. 3B, the suture retention strength increased as the silk/PLA fiber content increased in WMVGs due to the rigidity of the silk and PLA. Furthermore, all of the WMVGs showed superior suture retention strength as compared to mammary arteries and saphenous veins.

Figure 3C:
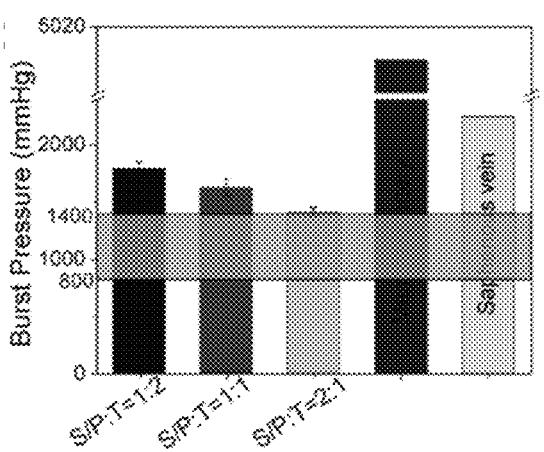

The burst pressure of WMVGs was evaluated to determine if the porous WMVGs would leak in a physiological environment. During the test, PBS was continuously injected into the samples and the Laplace pressure prevented the grafts from leaking. As shown in FIG. 3C, the WMVGs with a higher TPU content showed a higher burst pressure. Without being bound by theory, it is believed this was because the densely packed TPU nanofibers yielded a higher Laplace pressure. However, all WMVGs showed a lower burst pressure than mammary arteries and saphenous veins due to their porous structures. The burst pressure was expected to increase when the grafts were filled with cells. Nevertheless, the burst pressure of WMVGs still exceeded typical human physiological blood pressure (ranging from 800 mmHg to 1400 mmHg).

Figure 3D:
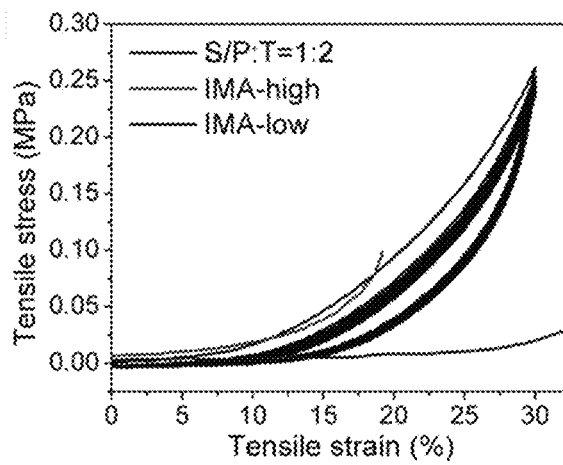
Figure 3E:
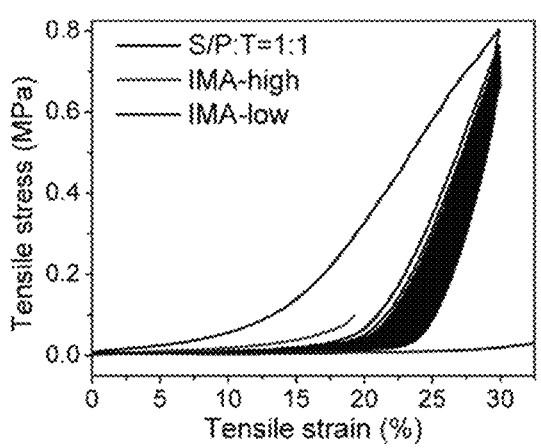
Figure 3F:
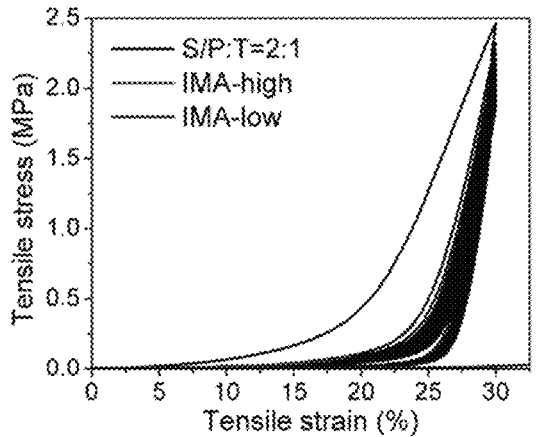

WMVGs were stretched and released for 50 cycles to determine their cyclic properties and were compared with human internal mammary artery (IMA) data from the literature as shown in FIGS. 3D-3F. WMVGs showed larger hysteresis loops in the first cycle than the latter cycles because the fibers loosened and reoriented in response to the external force. The cyclical stress-strain curves were all located within the upper (red curve) and lower (blue curve) bounds of the IMA data, indicating that the WMVGs exhibited the non-linear tensile stress-strain behavior of native human arteries. The biomimetic mechanical behavior of WMVGs was attributed to the synergistic effects of biomaterial combinations and the special wavy-structure of WMVGs.

Figure 4A:
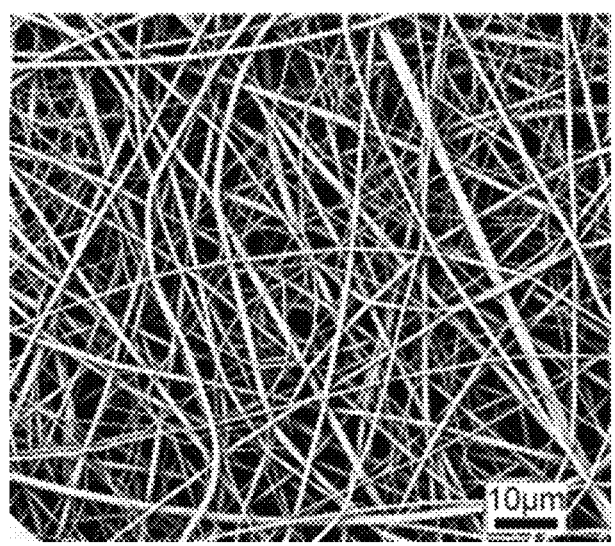
FIGS. 4A-4I depict scanning electron micrograph (SEM) images and X-ray photoelectron spectrometer (XPS) survey scans of silk/PLA fiber mat (S/P) (FIGS. 4A-4C), silk/PLA-dopamine (S/P-DA) fiber mat (FIGS. 4D-4F) and silk/PLA-dopamine & heparin (S/P-D&H) fiber mat (FIGS. 4G-4I).
Figure 4B:
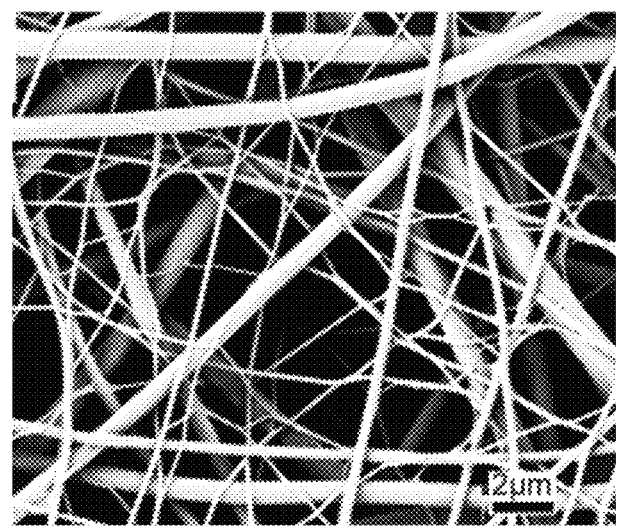
Figure 4C:
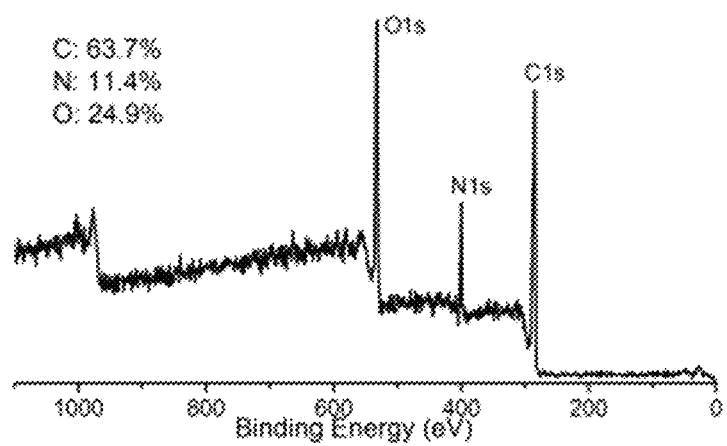
Figure 4D:
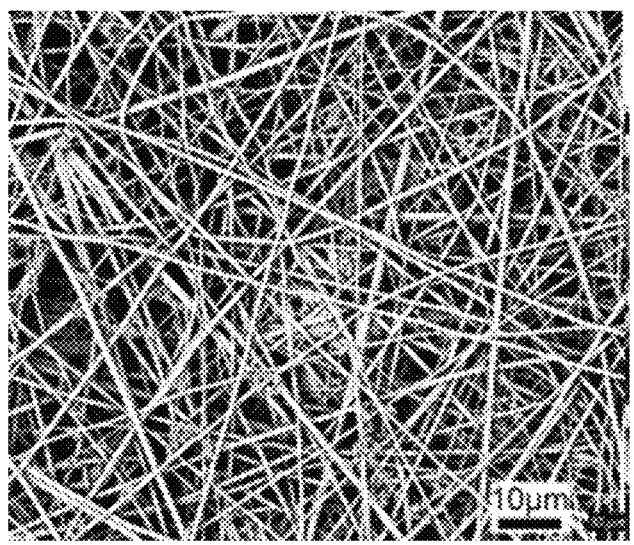
Figure 4E:
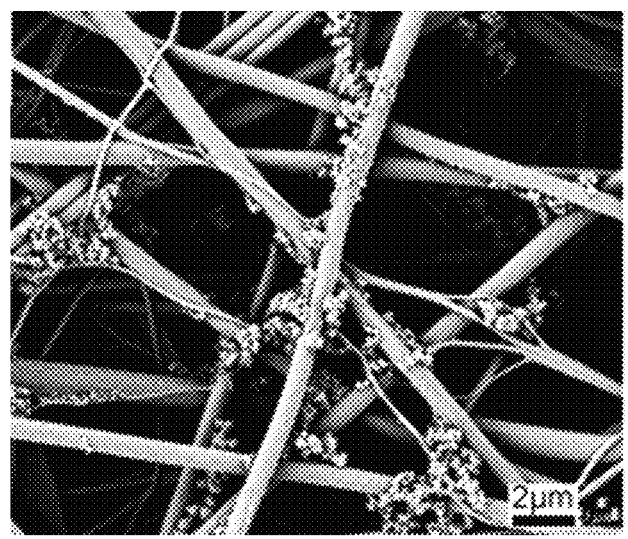
Figure 4F:
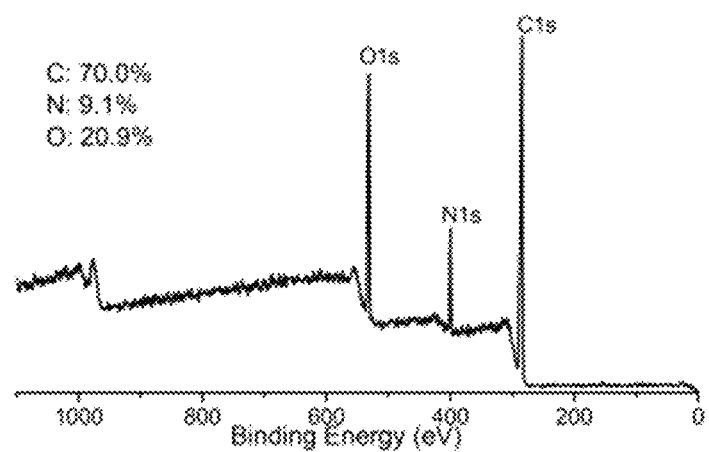
Figure 4G:
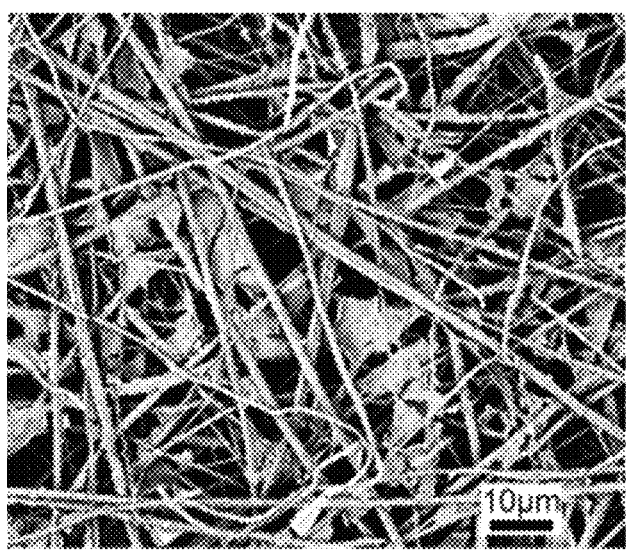
Figure 4H:
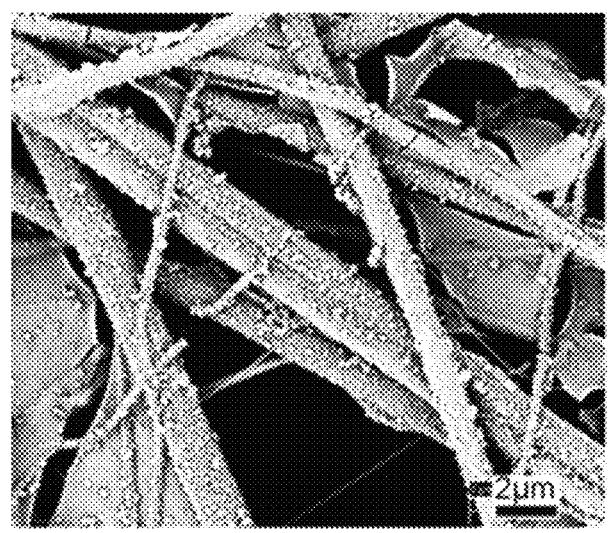
Figure 4I:
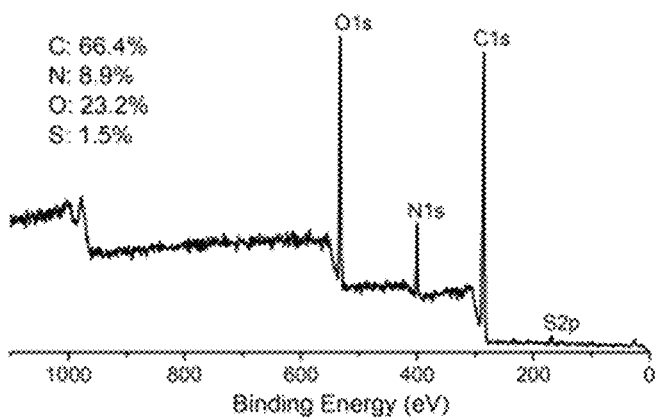

Modification using dopamine and heparin were employed to enhance the endothelial cell affinity and antithrombogenicity of the inner silk/PLA layer. FIG. 4 shows the morphology and XPS spectra of modified silk/PLA fibers. The as-spun silk/PLA fibers exhibited submicron-sized smooth fibers (FIGS. 4A & 4B). After dopamine modification, dopamine molecules were self-polymerized into submicron-sized particles and bonded onto silk/PLA fibers as shown in FIGS. 4D & 4E. XPS results (FIGS. 4C & 4F) indicated that the atom percentage of C increased after dopamine modification (FIG. 4F), which was mainly attributed to the aromatic ring of dopamine. After heparin coating, submicron heparin particles were uniformly attached to the silk/PLA fibers, and thin films also formed in some regions (FIGS. 4G & 4H). A percentage of 1.5% S element was detected on the XPS spectrum (FIG. 4I), thus indicating the successful coating of heparin on the silk/PLA fibers.

Figure 5A:
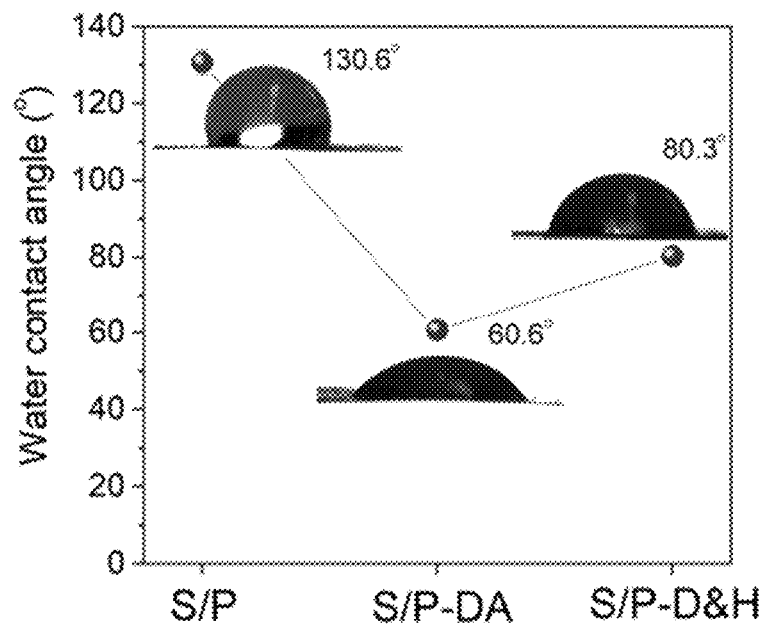
FIGS. 5A-5E depict wettability and platelet adhesion of fiber surfaces.
Figure 5B:
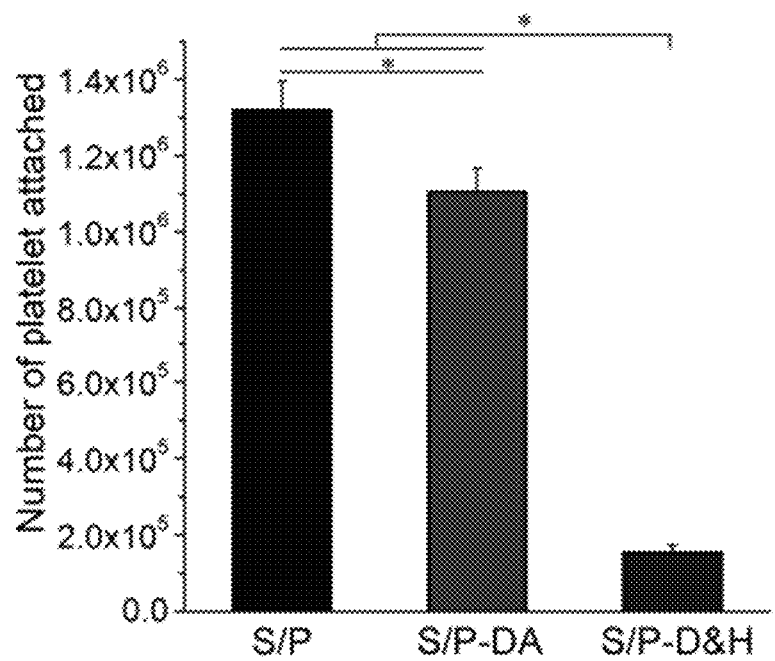
Figure 5C:
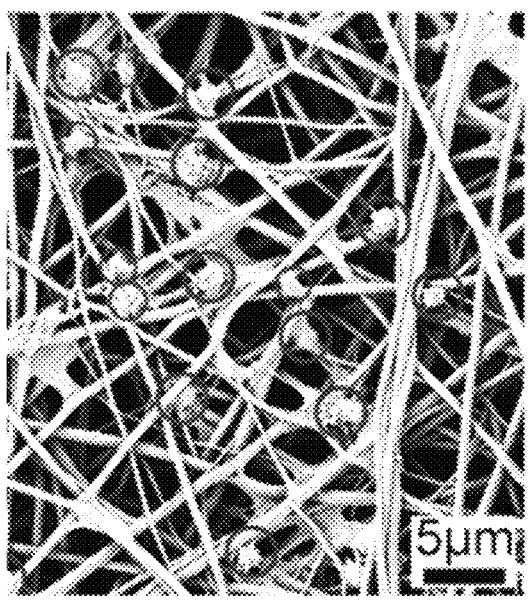
Figure 5D:
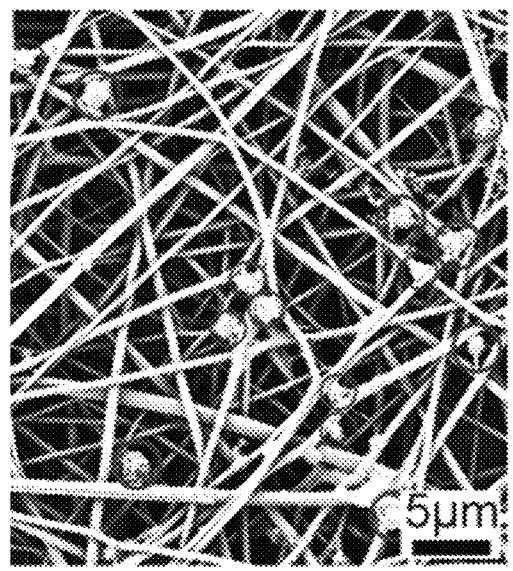
Figure 5E:
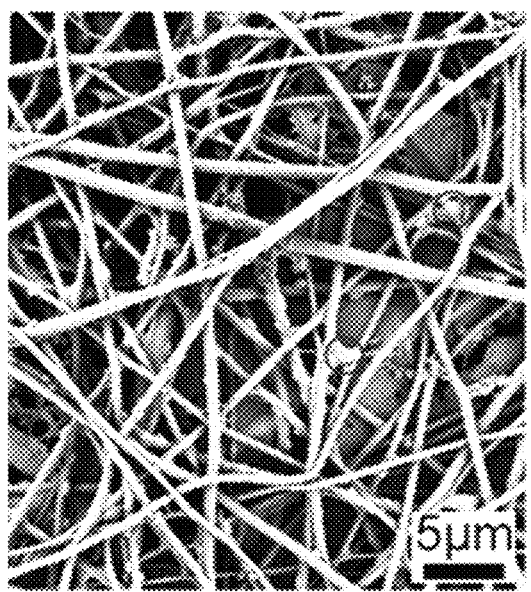

The water contact angle results (FIG. 5A) showed that the hydrophilicity was dramatically enhanced after dopamine coating, while the contact angle of SIP-D&H was higher than S/P-DA. Although both dopamine and heparin are highly hydrophilic molecules, the significantly increased roughness of the SIP-D&H fiber surface prevented water penetration. Nevertheless, both modified silk/PLA fiber mats were hydrophilic while the as-spun, un-modified silk/PLA (S/P) fiber mat was highly hydrophobic. The platelet adhesion test results (FIG. 5B) showed that the number of attached platelets decreased greatly when heparin was coated onto the fiber surface. From the SEM images, platelets mostly appeared round in shape and adhered to the fibers, especially at the intersections of multiple fibers. Some platelets on the unmodified silk/PLA fiber mat displayed a flat shape, thus implying a high thrombosis risk (FIG. 5C). The number of platelets decreased on the S/P-DA fiber mat and flat platelets were absent (FIG. 5D). Remarkably, platelets were barely present on the S/P-D&H fiber mat, indicating high antithrombogenicity (FIG. E).

Figure 6A:
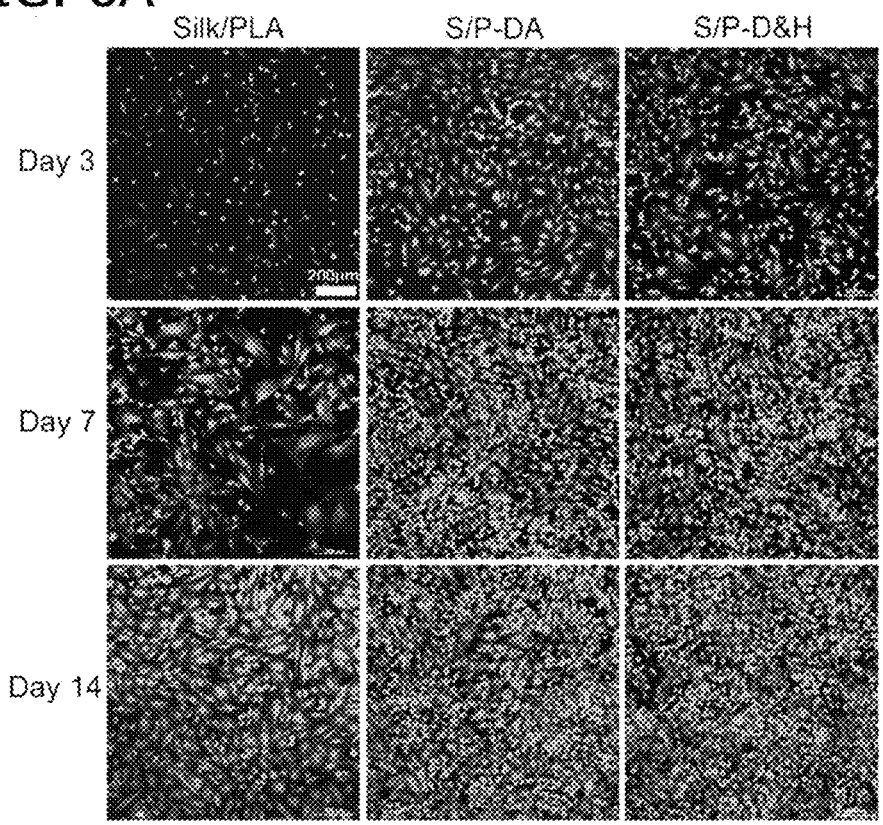
FIGS. 6A-6C depict culture of cells on S/P fiber mats.
Figure 6B:
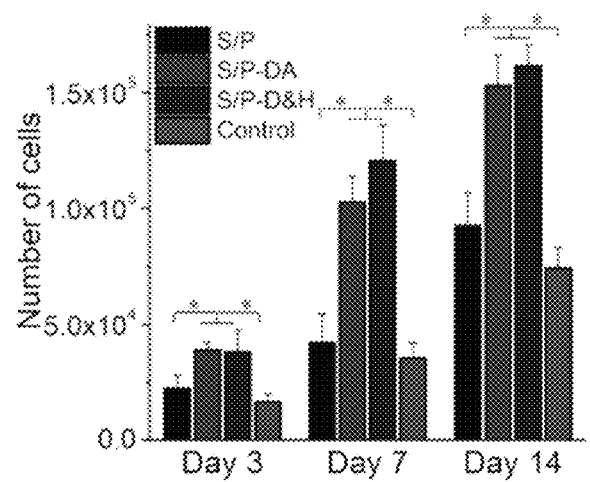
Figure 6C:
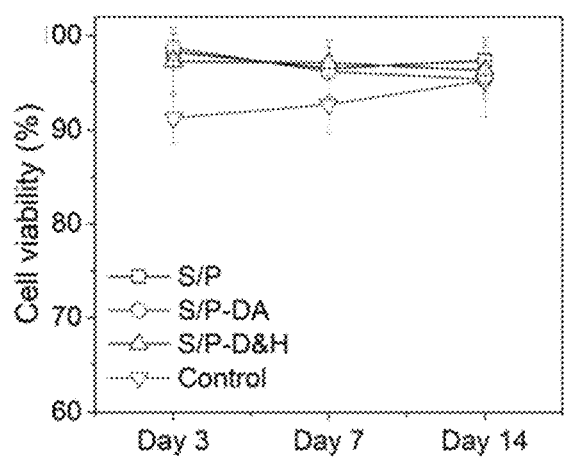

HUVECs were cultured on modified silk/PLA fiber mats for up to 14 days. Immunofluorescence images from the live/dead assay (FIG. 6A) showed that HUVECs were able to attach and proliferate on all fiber mats, indicating that the fiber mats were all biocompatible with HUVECs. The MTS data (FIG. 6B) showed that S/P-DA and S/P-D&H samples had significantly higher cell populations than silk/PLA samples and control groups, while the difference between S/P-DA and S/P-D&H was not statistically significant. This indicated that the introduction of dopamine enhanced endothelial cell affinity, while the addition of heparin did not further improve endothelial cell affinity. In addition, the cell population increased more than two times from day 3 to day 7 for all samples, while the improvement from day 7 to day 14 was smaller for S/P-DA and S/P-D&H compared to silk/PLA. Presumably because cells already covered almost all of the available area on day 7 on S/P-DA and S/P-D&H, as indicated in FIG. 6A. Moreover, all three fiber mats showed high cell viability (over 95%), as shown in FIG. 6C.

Figure 7A:
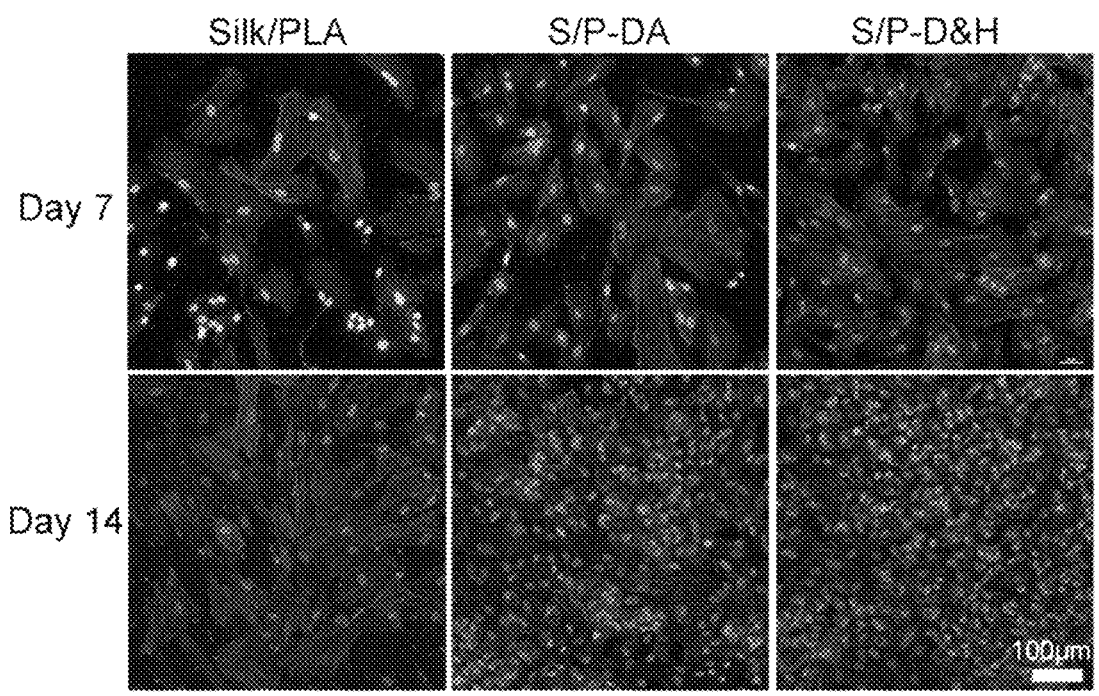
FIGS. 7A-7B depict cytoskeletal morphology (FIG. 7A) and cellular morphology (FIG. 7B) of HUVECs cultured on differently modified silk/PLA.
Figure 11A:
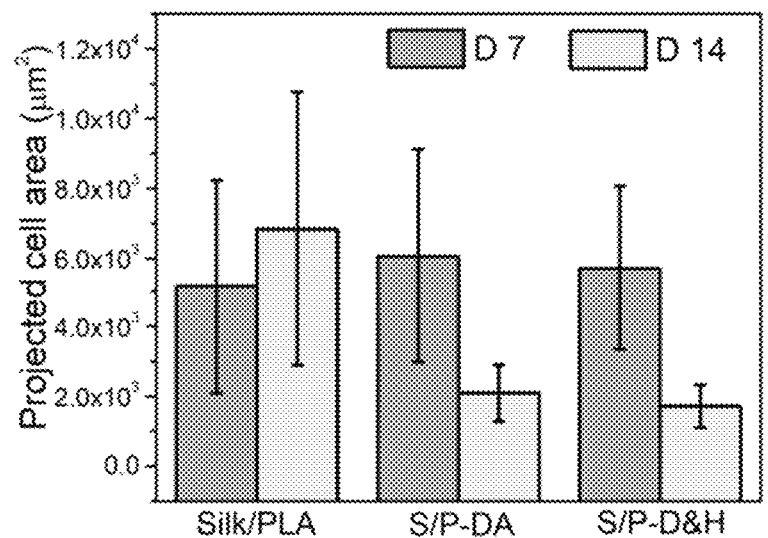
FIGS. 11A and 11B depict statistical data of cytoskeleton morphology images.
Figure 11B:
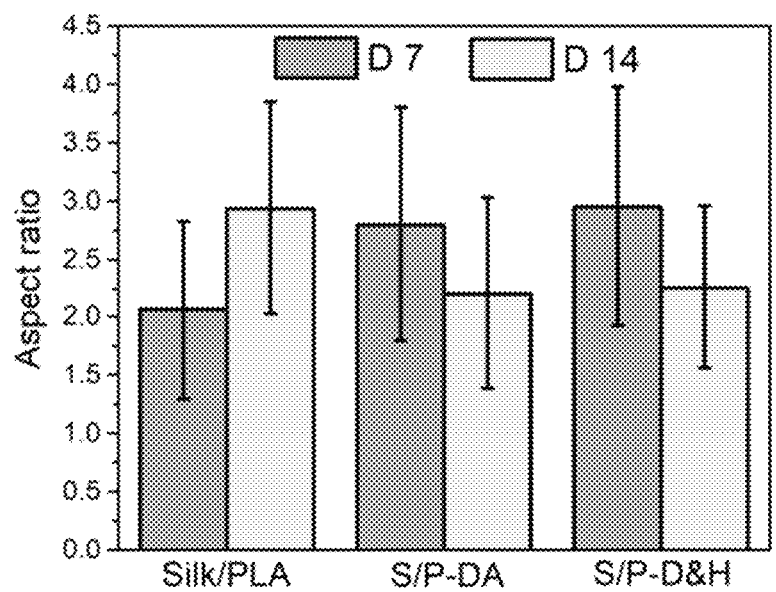

The cell phenotype was investigated using phalloidin/DAPI immunofluorescence staining and SEM. The cytoskeletons of HUVECs cultured on modified fiber mats are shown in the fluorescence images (FIG. 7A). Cells on all materials showed a spread morphology with clear fibrils indicating a healthy growing state. The cell proliferation showed the same trend as the MTS and live/dead assays. FIGS. 11A and 11B depict measurements of the projected cell area (FIG. 11A) and the cell aspect ratio (FIG. 11B). The results indicated that the cells on S/P-DA and S/P-D&H were larger and more spread out than the cells on silk/PLA at day 7. At day 14, the area and aspect ratio of the cells on S/P-DA and S/P-D&H decreased due to the significantly increased cell population; however, the cells on silk/PLA were more spread out compared to day 7.

Figure 7B:
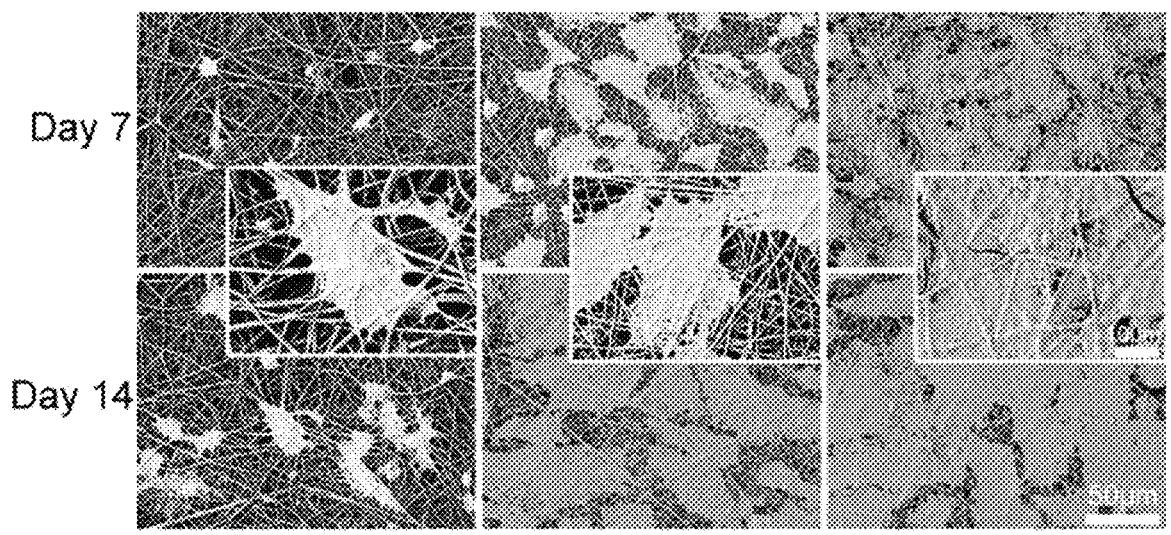

Cell-substrate interactions were analyzed using SEM. As shown in FIG. 7B, HUVECs showed a flat shape on all fiber mats, while the cell size and area for the cells on silk/PLA were smaller than the cells on S/P-DA and S/P-D&H. The cells were tightly bonded to the fibers with pseudopodia extending out, indicating that the cells were able to freely migrate on these materials. The HUVECs on S/P-DA and S/P-D&H covered almost the whole substrate after 14 days of culture. This indicated that endothelial cells quickly formed a cell layer on the modified silk/PLA fibers, which would be beneficial for further improving the material's mechanical properties (e.g. improving burst pressure) and preventing thromboses.

Figure 8:
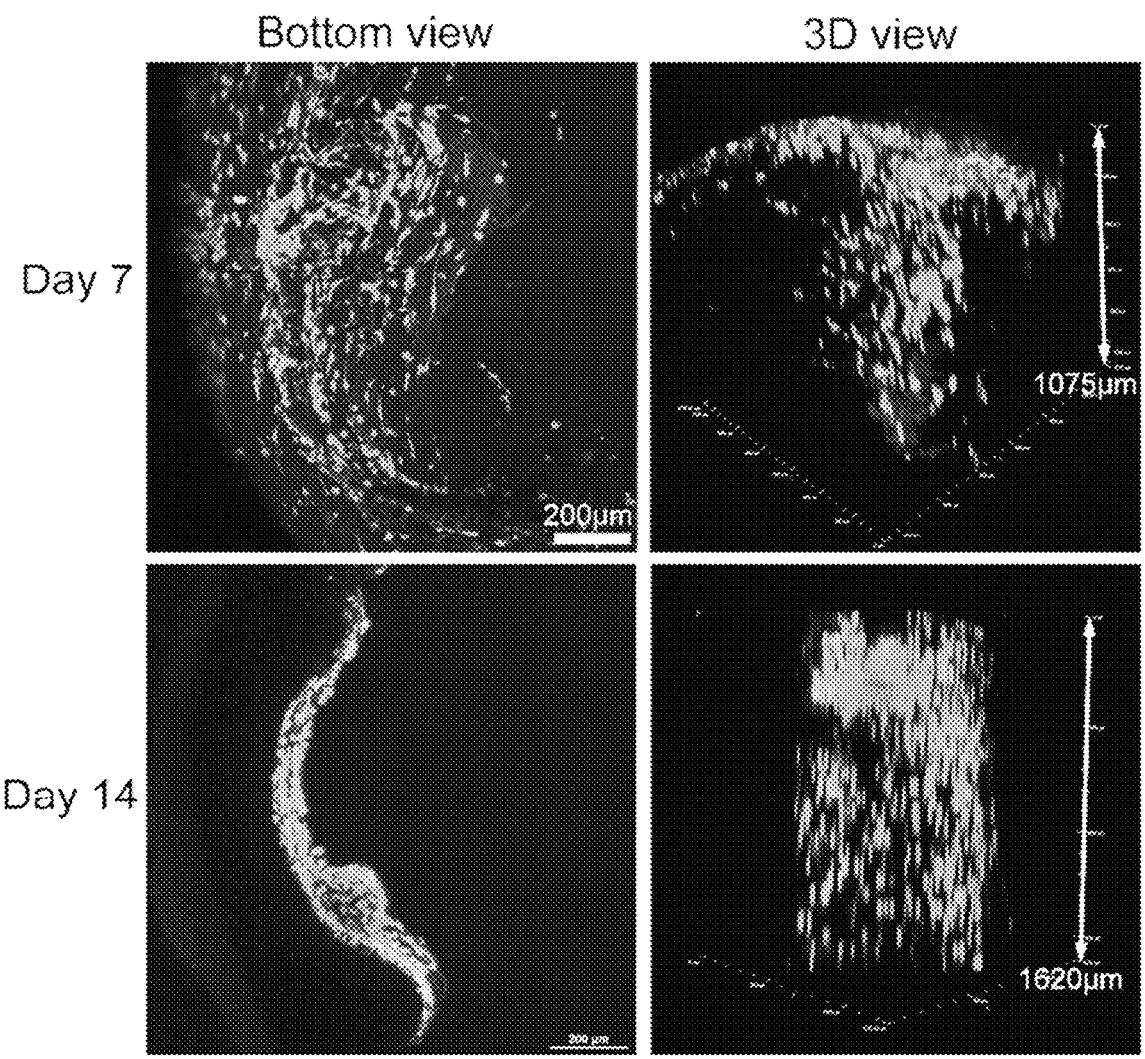
FIG. 8 depicts confocal fluorescence images of HUVECs cultured on dopamine- and heparin-modified WMVGs for 7 and 14 days. Cells were stained with calcein-AM (green) and EthD-1 (red).

To investigate whether endothelial cells were able to migrate on tubular grafts, the inner surface of WMVGs were modified with dopamine and heparin and then seeded with HUVECs for up to 14 days. As shown in FIG. 8, HUVECs were able to migrate upward in the lumen of the WMVG, although the cells were cultured in a stationary state. Cells were mostly present at the bottom of the WMVG at day 7 and the depth of cell coverage was 1075 μm. By day 14, cells had migrated upwards and were more uniformly distributed across the tube compared to day 7. The depth of cell coverage increased to 1620 μm and the cell population also greatly increased. Moreover, the cells maintained high viability. These results indicated that the modified WMVGs had excellent endothelial cell affinity and could stimulate fast endothelialization on the lumen side of the WMVGs.

Figure 3G:
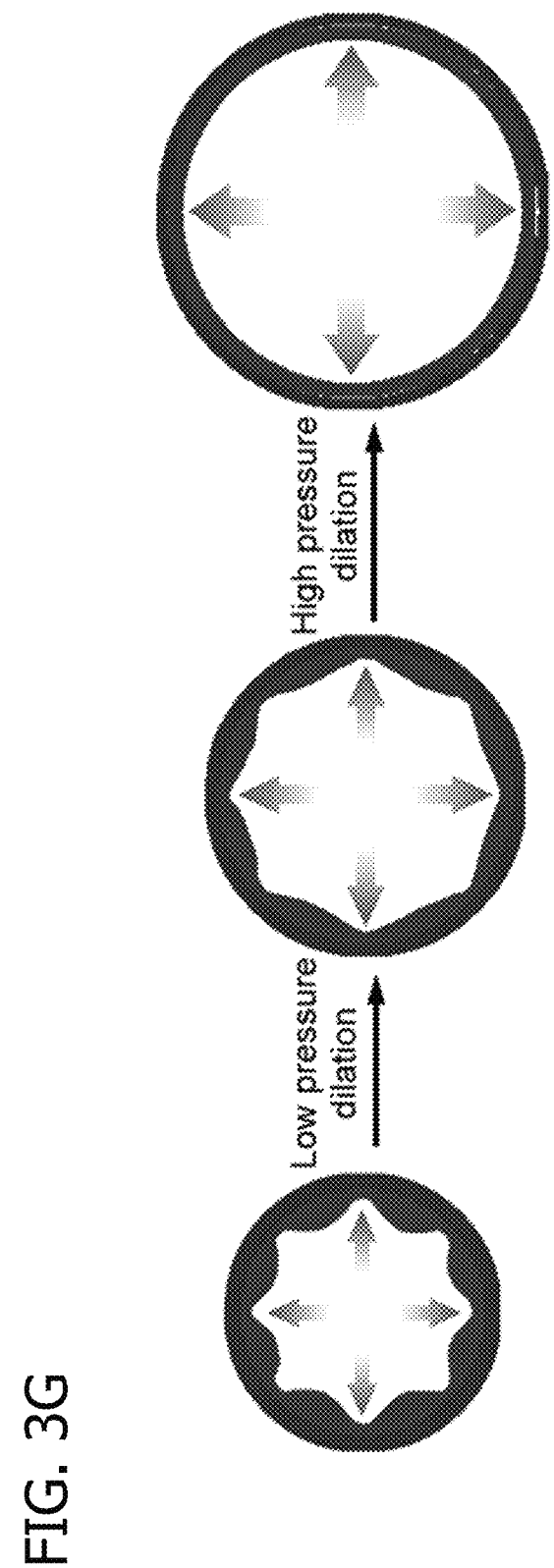

Effectively preventing thromboses and stimulating fast endothelialization of small diameter vascular grafts remain as critical challenges for artificial SDVGs. Due to the complexity of the structure and composition of blood vessels, it is difficult to mimic their special non-linear tensile stress-strain relationship using only a single biomaterial. Previously, different biomaterials and fabrication methods were combined to prepare multiple-layered SDVGs with different materials and structures in each layer. Although the triple-layered structure and the non-linear tensile stress-strain relationship of native blood vessels has been mimicked, the characteristics of the "toe region" has been difficult to achieve. The present disclosure provides a new method and material combination that closely resembles the microstructure and physiological properties of native blood vessels. Silk and PLA are both highly biocompatible and biodegradable materials with high moduli that can resemble the stiffer collagen component of blood vessels. Highly elastic TPU as a biocompatible elastomer is capable of resembling the elastin component of blood vessels. However, simply blending them together would result in a composite whose mechanical properties would lie somewhere in-between. It is known that, while less-wavy elastin plays a major role at low dilation pressures in native blood vessels, collagen fibrils eventually provide the needed strength at high dilation pressures. To achieve this property, a special design for the wavy inner layer was used. The wavy structure mimics the biological configuration of native blood vessels and provides a "toe region" in single-layered WMVGs. The performance of the WMVGs of the present disclosure was further enhanced by using multiple materials with properties similar to the components in native blood vessels. As illustrated in FIG. 3G, at low pressure, the wavy silk/PLA fibers oriented and aligned in the same fashion as collagen in blood vessels. The elasticity and recoverability were provided by the elastic TPU layer, which corresponded to the initial "toe region" of native blood vessels. The rigid silk/PLA layer starts to play a major role when the pressure increases further. Through this unique structure, design, and material combination, the special non-linear tensile stress-strain relationship of native blood vessels was successfully mimicked.

Surprisingly, the silk/PLA solution of the present disclosure resulted in loosely packed fibers due to silk's electrostatic charge. This special fibrous structure should facilitate cell penetration and tissue regeneration. One common problem faced by electrospinning SDVGs is the removal of samples from the mandrel without interfering with their delicate microstructure. Various methods such as using grease and winding the mandrel with copper wire have been used to assist with graft removal. With the assembled mandrel used in the method of the present disclosure, WMVGs were easily removed by pulling out the central tube first. However, the silk/PLA fibers tended to stick to the satellite cylinders due to electrostatic adhesion. Therefore, a thin PEO layer was electrospun first to assist with removing and harvesting the grafts.

After achieving the biomimetic mechanical properties of the WMVGs, the antithrombogenicity and endothelial cell affinity was determined. Although silk fibroin has been recognized as the most suitable biodegradable material for vascular grafts, its biocompatibility was further enhanced by incorporating biomolecules as described in the present disclosure. The results of modifying WMVGs by introducing dopamine showed that the HUVEC proliferation rate almost doubled after dopamine coating, and the cells also showed better cell-substrate interactions. The whole substrate was covered by an endothelial cell membrane within 14 days of culture. However, if WMVGs were directly implanted without pre-seeding with endothelial cells, thrombosis may occur since both silk/PLA and S/P-DA showed high platelet adhesion (FIGS. 5B and 5C). Further modification with heparin after dopamine coating dramatically reduced the number of attached platelets and improved antithrombogenicity. Moreover, the fibers modified with dopamine and heparin showed excellent endothelial cell affinity. Therefore, the modified WMVGs can be directly implanted without the need for pre-seeding endothelial cells. Although the heparin may be gradually released in vivo, the WMVG lumen surface should be rapidly covered by an endothelial cell membrane due to the greatly enhanced endothelial cell affinity.

The enhanced endothelial cell affinity was also demonstrated by the rapid migration of endothelial cells on stationary cultured WMVGs. A specially designed bioreactor is generally required for cell culture on vascular grafts since endothelial cells may find it difficult to migrate on tubular grafts when cultured in a stationary state and under the influence of gravity. Endothelial cells were able to migrate upward on the modified WMVG of the present disclosure in a stationary state due to the high cell affinity of the substrate without the need for any specially designed bioreactor. Therefore, small diameter vascular grafts (SDVG) of the present disclosure closely resemble the non-linear tensile stress-strain relationship of native blood vessels and possesses excellent endothelial cell affinity and antithrombogenicity.

The present disclosure provides a novel wavy, multi-component vascular graft (WMVG) with a wavy silk/PLA inner layer and an elastic TPU outer layer via electrospinning using a special assembled collector. The fabricated WMVG closely mimicked the non-linear tensile stress-strain relationship of native blood vessels and showed sufficient mechanical strength needed for implantation. Modification of the silk/PLA fibers with dopamine and heparin not only greatly enhanced endothelial cell migration and proliferation, but also gave the grafts antithrombogenicity. The WMVGs, which have biomimetic mechanical properties and endothelial cell affinity, can be mass produced, thus greatly reducing the treatment cost of CVD while increasing treatment efficacy.

What is claimed is:

1. A wavy multi-component vascular graft comprising an inner layer comprising
   rigid polymer fibers comprising silk and poly (lactic acid) (PLA)-and an outer layer comprising elastic polymer fibers selected from the group consisting of thermoplastic polyurethane (TPU), polyglycerol sebacate (PGS), poly (ester urethane) urea (PEUU), and combinations thereof;
   wherein the outer layer provides the outermost surface of the wavy multicomponent vascular graft.

2. The wavy multi-component vascular graft of claim 1 wherein the rigid polymer fibers comprise submicron diameter fibers.

3. The wavy multi-component vascular graft of claim 1 wherein the rigid polymer fibers comprise an average fiber diameter ranging from about 100 nm to about 1000 nm.

4. The wavy multi-component vascular graft of claim 1 wherein the elastic polymer fibers comprise nanoscale diameter fibers and submicron diameter fibers.

5. The wavy multi-component vascular graft of claim 1 wherein the elastic polymer fibers comprise an average fiber diameter ranging from about 50 nm to about 300 nm.

6. The wavy multi-component vascular graft of claim 1 further comprising a biomolecule.

7. The wavy multi-component vascular graft of claim 1 further comprising a cell.

8. The wavy multi-component vascular graft of claim 1 comprising a lumen diameter less than 6 mm.

9. The wavy multi-component vascular graft of claim 1 comprising a wall thickness ranging from about 200 μm to about 500 μm.

10. The wavy multi-component vascular graft of claim 1 comprising a suture retention strength ranging from about 1 N to about 4 N.

11. A method for preparing the wavy multi-component vascular graft of claim 1, the method comprising:
    electrospinning a first solution comprising a water soluble polymer material to form a first water soluble fiber;
    collecting the first water soluble fiber on an assembled mandrel that comprises a central tube and a plurality of satellite cylinders surrounding the tube to form a first water soluble fiber layer;
    electro-spinning a second solution comprising a rigid polymer material comprising PLA and silk to form a second fiber;
    collecting the second fibers on the first water soluble fiber layer to form an inner rigid polymer fiber layer;
    electrospinning a third solution comprising an elastic polymer material comprising TPU, PGS, PEUU or a combination thereof to form a third fiber;
    collecting the third fibers on the rigid polymer fiber layer on the assembled mandrel to form an outer elastic polymer fiber layer; and
    removing the assembled mandrel to form a wavy multi-component vascular graft.

12. The method of claim 11 further comprising removing the water soluble fiber layer.

13. The method of claim 11 wherein the second solution and the third solution have a volume ratio ranging from about 1:2 to about 2:1.

14. The method of claim 11, wherein the inner rigid polymer fiber layer is modified with a biomolecule.

15. The method of claim 14, wherein the biomolecule is selected from the group consisting of dopamine, heparin, cell adhesion molecules, growth factors, chemokines, anti-coagulants, and combinations thereof.

16. The method of claim 11 further comprising seeding a cell on the wavy multi-component vascular graft.

17. The method of claim 16, wherein the cell is selected from the group consisting of an endothelial cell, a smooth muscle cell, a mesenchymal stem cell, a fibroblast cell, and combinations thereof.

* * * * *

SEQUENCE LISTING

```
<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1
```

```
Arg Gly Asp Ser
1

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Tyr Ile Gly Ser Arg
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic

<400> SEQUENCE: 3

Pro Asp Ser Gly Arg
1               5

<210> SEQ ID NO 4
<211> LENGTH: 4
<212> TYPE: PRT
<213> ORGANISM: Artificial Sequence
<220> FEATURE:
<223> OTHER INFORMATION: Synthetic

<400> SEQUENCE: 4

Arg Gly Asp Val
1
```